(12) United States Patent
Li et al.

(10) Patent No.: US 7,344,863 B2
(45) Date of Patent: *Mar. 18, 2008

(54) METHODS FOR PRODUCING POLYPEPTIDES THROUGH ENHANCED SYNTHESIS OF ENCODING NUCLEIC ACID MOLECULES

(75) Inventors: Wu-Bo Li, Gaithersburg, MD (US); Joel A. Jessee, Mount Airy, MD (US); David Schuster, Poolesville, MD (US); Jiulin Xia, Germantown, MD (US); Gulilat Gebeyehu, Potomac, MD (US)

(73) Assignee: Invitrogen Corporation, Carlsbad, CA (US)

( * ) Notice: Subject to any disclaimer, the term of this patent is extended or adjusted under 35 U.S.C. 154(b) by 584 days.

This patent is subject to a terminal disclaimer.

(21) Appl. No.: 10/899,139

(22) Filed: Jul. 27, 2004

(65) Prior Publication Data

US 2004/0265969 A1    Dec. 30, 2004

Related U.S. Application Data

(63) Continuation of application No. 09/266,935, filed on Mar. 12, 1999, now Pat. No. 6,787,305.

(60) Provisional application No. 60/077,881, filed on Mar. 13, 1998.

(51) Int. Cl.
*C12P 21/00* (2006.01)
*C12P 19/34* (2006.01)

(52) U.S. Cl. ..................... 435/70.1; 435/91.1
(58) Field of Classification Search ............. None
See application file for complete search history.

(56) References Cited

U.S. PATENT DOCUMENTS

| | | | |
|---|---|---|---|
| 4,683,202 A | 7/1987 | Mullis | |
| 4,767,699 A | 8/1988 | Vary et al. | |
| 4,800,159 A | 1/1989 | Mullis et al. | |
| 5,165,925 A | 11/1992 | Leong | |
| 5,187,085 A | 2/1993 | Lee | |
| 5,350,672 A | 9/1994 | Oberst et al. | |
| 5,484,702 A | 1/1996 | Ludwig | |
| 5,500,356 A | 3/1996 | Li et al. | |
| 5,545,540 A | 8/1996 | Mian | |
| 5,759,778 A | 6/1998 | Li et al. | |
| 5,871,929 A | 2/1999 | Barnes | |
| 6,013,488 A | 1/2000 | Hayashizaki | |
| 6,268,133 B1 | 7/2001 | Nisson et al. | |
| 6,787,305 B1 | 9/2004 | Li et al. | |

FOREIGN PATENT DOCUMENTS

| | | |
|---|---|---|
| DE | 44 11 588 C1 | 9/1995 |
| DE | 44 11 594 C1 | 12/1995 |
| EP | 0 821 058 A2 | 1/1998 |
| EP | 0 821 059 A2 | 1/1998 |
| EP | 0 726 310 B1 | 7/2003 |
| WO | WO 95/20682 | 8/1995 |
| WO | WO 99/41410 | 8/1999 |

OTHER PUBLICATIONS

LaVallie et al., Gene fusion expression systems in *Escherichia coil*, Current Opinion in Biotechnology 1995, 6:501-506.*
Aslanyan, V.M., et al., "Conformation and Thermal Stability of DNA in Aqueous Solutions of β-Alanine and γ-Aminobutyric Acid," *Biophysics* 29:615-620, Pergamon Press (1984).
Buche, A., et al., "Glycine and other amino compounds prevent chromatin precipitation at physiological ionic strength," *FEBS Lett.* 247:367-370, Elsevier Science B.V. (1989).
Buche, A., et al., "Organic Osmotic Effectors and Chromatin Structure," *J. Biomol. Struct. & Dynam.* 8:601-618, Adenine Press (1990).
Buche, A., et al., "Effect of Organic Effectors on Chromatin Solubility, DNA-Histone H1 Interactions, DNA and Histone H1 Structures," *J. Biomol. Struct. & Dynam.* 11:95-119, Adenine Press (1993).
Cánovas, D., et al., Osmoprotectants in *Halomonas elongata*: High-Affinity Betaine Transport System and Choline-Betaine Pathway, *J. Bacteriol.* 178:7221-7226, American Society for Microbiology (1996).
Cánovas, D., et al., "Isolation and Characterization of Salt-sensitive Mutants of the Moderate Halophile *Halomonas elongata* and Cloning of the Ectoine Synthesis Genes," *J. Biol. Chem.* 272:25794-25801, American Society for Biochemistry and Molecular Biology (Oct. 1997).

(Continued)

*Primary Examiner*—Gary Benzion
*Assistant Examiner*—Mark Staples

(57) ABSTRACT

The present invention is directed to compositions and methods for enhancing synthesis of nucleic acid molecules, particularly GC-rich nucleic acid molecules. Specifically, the invention provides compositions comprising one or more nitrogen-containing organic compounds having a formula selected from the group consisting of formula I and formula II (or salts or derivatives thereof), preferably 4-methylmorpholine N-oxide or betaine (carboxymethyltrimethylammonium), and further comprising one or more compounds selected from the group consisting of proline and an N-alkylimidazole compound, and more preferably proline, 1-methylimidazole or 4-methylimidazole. The invention further relates to methods for enhanced, high-fidelity synthesis of nucleic acid molecules, including via amplification (particularly PCR), reverse transcription, and sequencing methods. The invention also relates to nucleic acid molecules synthesized by these methods, to fragments or derivatives thereof, and to vectors and host cells comprising such nucleic acid molecules, fragments, or derivatives. The invention also relates to kits for synthesizing, amplifying, reverse transcribing or sequencing nucleic acid molecules comprising one or more of the compositions of the invention.

14 Claims, 13 Drawing Sheets

OTHER PUBLICATIONS

Carninci, P., et al., "Thermostabilization and thermoactivation of thermolabile enzymes by trehalose and its application for the synthesis of full length cDNA," *Proc. Natl. Acad. Sci. USA 95*:520-524, National Academy of Sciences (Jan. 1998).

Chambers, S. T., et al., "Dimethylthetin Can Substitute for Glycine Betaine as an Osmoprotectant Molecule for *Escherichia coli*," *J. Bacteriol. 169*:4845-4847, American Society for Microbiology (1987).

Flock, S., et al., "Osmotic Effectors and DNA Structure: Effect of Glycine on Precipitation of DNA by Multivalent Cations." *J. Biomol. Struct. & Dynam. 13*:87-102, Adenine Press (1995).

Flock, S., et al., "Dielectric Constant and Ionic Strength Effects on DNA Precipitation," *Biophys. J. 70*:1456-1465, Biophysical Society (1996).

Flock, S., et al., "$^{23}$Na NMR Study of the Effect of Organic Osmolytes on DNA Counterion Atmosphere," *Biophys. J. 71*:1519-1529, Biophysical Society (1996).

Frackman, S., et al., "Betaine and DMSO: Enhancing Agents for PCR," *Promega Notes 65*:27-29, Promega (Feb. 1998).

Gouesbet, G., et al., "Characterization of the *Erwinia chrysanthemi* Osmoprotectant Transporter Gene *ousA*," *J. Bacteriol. 178*:447-455, American Society for Microbiology (1996).

Hengen, P.N., "Optimizing multiplex and LA-PCR with betaine," *Trends Biochem. Sci. 22*:225-226, Elsevier Trends Journal (Jun. 1997).

Henke, W., et al., "Betaine improves the PCR amplification of GC-rich DNA sequences," *Nucl. Acids Res. 25*:3957-3958, Oxford University Press (Oct. 1997).

Hogrefe, H., et al., "Novel PCR Enhancing Factor Improves Performance of *Pfu* DNA Polymerase," *Stratagene Strategies 10*:93-96, Stratagene (Aug. 1997).

Houssier, C., et al., "Effects of Compensatory Solutes on DNA and Chromatin Structural Organization in Solution," *Comp. Biochem. Physiol. 117A*:313-318, Elsevier Science Inc. (Jul. 1997).

Iakobashvili, R. and Lapidot, A., "Low temperature cycled PCR protocol for Klenow fragment of DNA polymerase I in the presence of proline," *Nucl. Acids Res. 27*:1566-1568, Oxford University Press (Mar. 1999).

Instruction Manual for "GeneTrapper™ cDNA Positive Selection System," Catalog No. 10356-020, GIBCO BRL, Life Technologies, Gaithersburg, MD.

Jakob, R. and Saenger, W., "Reversed-phase ion-pair chromatographic separation of ribulose 1,5-biphosphate from 3-phosphoglycerate and its application as a new enzyme assay for RuBP carboxylase/oxygenase," *FEBS Letters 183*:111-114, Elsevier Science B.V. (1985).

Joung, et al., "Mutations in two Cysteine-hystidine-rich clusters in adenovirus type 2 DNA affect DNA binding," *J. Virol. 66*:5788-5796, American Society for Microbiology (1992).

Kondakova, N.V., et al., "Effect of Low-molecular Amines on the Conformation and Stability of the DNA Double Helix," *Molekulyamaya Biologiya 9*:742-746, Izdatelstvo Nauka, translated into English and cited in *Molecular Biology*, pp. 593-596, translated by the Consultants Bureau (1975).

Landre, P.A., et al., "The Use of Cosolvents to Enhance Amplification by the Polymerase Chain Reaction," in: *PCR Strategies*, Innis, M.A. et al., eds., Academic Press, San Diego, pp. 3-16 (1995).

Le Rudulier, D., et al., "Molecular Biology of Osmoregulation," *Science 224*:1064-1068, American Association for the Advancement of Science (1984).

Li, C.-J., et al., "Nonprotein Amino Acids from Seeds of *Cycas circinalis* and *Phaseolus vulgaris*," *Phytochem. 42*:443-445, Pergamon Press (1996).

Malin, G. and A. Lapidot, "Induction of Synthesis of Tetrahydropyrimidine Derivatives in *Streptomyces* Strains and Their Effect on *Escherichia coli* in Response to Osmotic and Heat Stress," *J. Bacteriol. 178*:385-395, American Society for Microbiology (1996).

Marquet, R. and C. Houssier, "Thermodynamics of Cation-Induced DNA Condensation," *J. Biomol. Struct. & Dynam. 9*:159-167, Adenine Press (1991).

Mytelka, D.S. and M.J. Chamberlin, "Analysis and suppression of DNA polymerase pauses associated with a trinucleotide consensus," *Nucl. Acids Res. 24*:2774-2781, Oxford University Press (1996).

Panaccio, M., et al., "FoLT PCR: A Simple PCR Protocol for Amplifying DNA Directly from Whole Blood," *BioTech. 14*:238-243, Eaton Publishing Co. (1993).

Rafferty, J.A. and Fletcher, H.L., "Sequence Analysis of a Family of Highly Repeated DNA Units in *Stauroderus scalaris* (Orthoptera)," *Intl. J. Genome Res. 1*:1-16, World Scientific (1992).

Rajendrakumar, C.S.V., et al., "DNA helix destabilization by proline and betaine: possible role in the salinity tolerance process," *FEBS Lett. 410*:201-205, Federation of European Biomedical Societies (Jun. 1997).

Randall, K., et al., "Natural and syntheic betaines counter the effects of high NaCl and urea concentrations," *Biochim. Biophys. Acta 1291*:189-194, Elsevier (1996).

Randall, K., et al., "Accumulation of natural and synthetic betaines by a mammalian renal cell line," Biochem. *Cell Biol. 74*:283-287, National Research Council of Canada (1996).

Rees, W.A., et al., "Betaine Can Eliminate the Base Pair Composition Dependence of DNA Melting," *Biochemistry 32*:137-144, American Chemical Society (1993).

Shepard, A.R. and Rae, J.L., "Magnetic Bead Capture of cDNAs from Double-Stranded Plasmid cDNA Libraries," *Nucl. Acids Res. 25*:3183-3185, Oxford University Press (Aug. 1997).

Solomon, "Chapter 24. Amino Acids and Proteins," in: *Organic Chemistry*, 5$^{th}$ Ed., John Wiley & Sons, Inc., pp. 1092-1098 (1992).

Urdea, M.S., "Branched DNA Signal Amplification," *Bio/Technology 12*:926,928, Nature Publishing Co. (1994).

Varadaraj, K. and D.M. Skinner, "Denaturants or cosolvents improve the specificity of PCR amplification of a G+C-rich DNA using genetically engineered DNA polymerases," *Gene 140*:1-5, Elsevier Science B.V.(1994).

Weissensteiner, T. and J.S. Lanchbury, "Strategy for Controlling Preferential Amplification and Avoiding False Negatives in PCR Typing," *BioTechniques 21*:1102-1108, Eaton Publishing Company (1996).

Woodford, K., et al., "The Use of K$^+$-free buffers eliminates a common cause of premature chain termination in PCR and PCR sequencing," *Nucl. Acids Res. 23*:539, Oxford University Press (1995).

Bioactive Peptides, 1993 Sigma Chemical Company Catalogue, St. Louis, MO, pp. 1028-1034 (1993).

Life Technologies, Inc., 1995-96 GIBCO/BRL product catalogue and reference guide, pp. 19-10 and 19-12 (1995-1996).

Derwent World Patents Index, Unverified English language abstract of DE 44 11 588 C1 (Document AM1), WPI Accession No. 10428036.

Derwent World Patents Index, Unverified English language abstract of DE 44 11 594 C1 (Document AN1), WPI Accession No. 10524091.

* cited by examiner

BETAINE MONOHYDRATE ([CARBOXYMETHYL] TRIMETHYLAMMONIUM)

CARNITINE ($\beta$-HYDROXY-$\gamma$-[TRIMETHYLAMMONIO]BUTERATE)

PROLINE

PIPECOLIC ACID (2-PIPERIDINECARBOXYLIC ACID)

ECTOINE (THP[B];[S]-2-METHYL-1,4,5,6-TETRAHYDRO-PYRIMIDINE-4-CARBOXYLIC ACID)

MMNO (4-METHYLMORPHOLINE-4-OXIDE)

TMANO (TIMETHYLAMINE N-OXIDE)

1-METHYLIMIDIZOLE

4(5)-METHYLIMIDIZOLE

METHODS FOR PRODUCING POLYPEPTIDES THROUGH ENHANCED SYNTHESIS OF ENCODING NUCLEIC ACID MOLECULES

CROSS REFERENCE TO RELATED APPLICATIONS

The present application is a continuation of U.S. application Ser. No. 09/266,935, filed Mar. 12, 1999, which claims the benefit of U.S. Provisional Application No. 60/077,881, filed Mar. 13, 1998, the disclosures of which applications are incorporated by reference herein in their entireties.

BACKGROUND OF THE INVENTION

1. Field of the Invention

The present invention is in the fields of molecular and cellular biology. The invention is related generally to compounds, compositions and methods useful in enhancing synthesis of nucleic acid molecules, especially from GC-rich nucleic acid templates. Specifically, the invention provides compositions comprising one or more compounds having a formula selected from the group consisting of formula I and formula II. Preferably used in accordance with the invention are 4-methylmorpholine N-oxide, betaine (carboxymethyl-trimethylammonium), any amino acid (or derivative thereof), and/or an N-alkylimidazole such as 1-methylimidazole or 4-methylimidazole. In a preferred aspect, two or more, three or more, four or more, etc. of the compounds of the invention are combined to facilitate nucleic acid synthesis.

The invention also relates to compositions comprising one or more compounds of the invention and one or more additional components selected from the group consisting of (i) one or more nucleic acid molecules (including nucleic acid templates), (ii) one or more nucleotides, (iii) one or more polymerases or reverse transcriptases, and (iv) one or more buffering salts.

These compounds and compositions of the invention may be used in methods for enhanced, high-fidelity synthesis of nucleic acid molecules, including via amplification (particularly PCR), reverse transcription, and sequencing methods. The invention also relates to nucleic acid molecules produced by these methods, to fragments or derivatives thereof, and to vectors and host cells comprising such nucleic acid molecules, fragments, or derivatives. The invention also relates to the use of such nucleic acid molecules to produce desired polypeptides. The invention also concerns kits comprising the compositions or compounds of the invention.

2. Related Art

Genomic DNA

In examining the structure and physiology of an organism, tissue or cell, it is often desirable to determine its genetic content. The genetic framework (i.e., the genome) of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene ultimately encodes. In order to produce a protein, a complementary copy of one strand of the DNA double helix (the "sense" strand) is produced by polymerase enzymes, resulting in a specific sequence of messenger ribonucleic acid (mRNA). This mRNA is then translated by the protein synthesis machinery of the cell, resulting in the production of the particular protein encoded by the gene. There are additional sequences in the genome that do not encode a protein (i.e., "noncoding" regions) which may serve a structural, regulatory, or unknown function. Thus, the genome of an organism or cell is the complete collection of protein-encoding genes together with intervening noncoding DNA sequences. Importantly, each somatic cell of a multicellular organism contains the full complement of genomic DNA of the organism, except in cases of focal infections or cancers, where one or more xenogeneic DNA sequences may be inserted into the genomic DNA of specific cells and not into other, non-infected, cells in the organism. As noted below, however, the expression of the genes making up the genomic DNA may vary between individual cells.

cDNA and cDNA Libraries

Within a given cell, tissue or organism, there exist myriad mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or hydroxyapatite, to which oligomers of deoxythymidine (dT) have been complexed. Since the 3' termini on all eukaryotic mRNA molecules contain a string of deoxyadenosine (dA) bases, and since dA binds to dT, the mRNA molecules can be rapidly purified from other molecules and substances in the tissue or cell extract. From these purified mRNA molecules, cDNA copies may be made using the enzyme reverse transcriptase, which results in the production of single-stranded cDNA molecules. The single-stranded cDNAs may then be converted into a complete double-stranded DNA copy of the original mRNA (and thus of the original double-stranded DNA sequence, encoding this mRNA, contained in the genome of the organism) by the action of a DNA polymerase. The protein-specific double-stranded cDNAs can then be inserted into a plasmid, which is then introduced into a host bacterial cell. The bacterial cells are then grown in culture media, resulting in a population of bacterial cells containing (or in many cases, expressing) the gene of interest.

This entire process, from isolation of mRNA to insertion of the cDNA into a plasmid to growth of bacterial populations containing the isolated gene, is termed "cDNA cloning." If cDNAs are prepared from a number of different mRNAs, the resulting set of cDNAs is called a "cDNA library," representing the different functional (i.e., expressed) genes present in the source cell, tissue or organism. Genotypic analysis of these cDNA libraries can yield much information on the structure and function of the organisms from which they were derived.

DNA Amplification

In order to increase the copy number of, or "amplify," specific sequences of DNA in a sample, investigators have relied on a number of amplification techniques. A commonly used amplification technique is the Polymerase Chain Reaction ("PCR") method described by Mullis and colleagues (U.S. Pat. Nos. 4,683,195; 4,683,202; and 4,800,159). This method uses "primer" sequences which are complementary to opposing regions on the DNA sequence to be amplified. These primers are added to the DNA target sample, along with a molar excess of nucleotide bases and a DNA polymerase (e.g., Taq polymerase), and the primers bind to their target via base-specific binding interactions (i.e., adenine binds to thymine, cytosine to guanine). By repeatedly passing the reaction mixture through cycles of increasing and decreasing temperatures (to allow dissociation of the two DNA strands on the target sequence, synthesis of complementary copies of each strand by the polymerase, and re-annealing of the new complementary strands), the copy number of a particular sequence of DNA may be rapidly increased.

Other techniques for amplification of target nucleic acid sequences have also been developed. For example, Walker et al. (U.S. Pat. No. 5,455,166; EP 0 684 315) described a method called Strand Displacement Amplification (SDA), which differs from PCR in that it operates at a single temperature and uses a polymerase/endonuclease combination of enzymes to generate single-stranded fragments of the target DNA sequence, which then serve as templates for the production of complementary DNA (cDNA) strands. An alternative amplification procedure, termed Nucleic Acid Sequence-Based Amplification (NASBA) was disclosed by Davey et al. (U.S. Pat. No. 5,409,818; EP 0 329 822). Similar to SDA, NASBA employs an isothermal reaction, but is based on the use of RNA primers for amplification rather than DNA primers as in PCR or SDA. Another known amplification procedure includes Promoter Ligation Activated Transcriptase (LAT) described by Berninger et al. (U.S. Pat. No. 5,194,370).

PCR-based DNA Fingerprinting

Despite the availability of a variety of amplification techniques, most DNA fingerprinting methods rely on PCR for amplification, taking advantage of the well-characterized protocols and automation available for this technique. Examples of these PCR-based fingerprinting techniques include Random Amplified Polymorphic DNA (RAPD) analysis (Williams, J. G. K. et al., *Nucl. Acids Res.* 18(22): 6531-6535 (1990)), Arbitrarily Primed PCR (AP-PCR; Welsh, J., and McClelland, M., *Nucl. Acids Res.* 18(24): 7213-7218 (1990)), DNA Amplification Fingerprinting (DAF; Caetano-Anollés et al., *Bio/Technology* 9:553-557 (1991)), and microsatellite PCR or Directed Amplification of Minisatellite-region DNA (DAMD; Heath, D. D. et al., *Nucl. Acids Res.* 21(24):5782-5785 (1993)). All of these methods are based on the amplification of random DNA fragments by PCR, using arbitrarily chosen primers.

DNA Sequencing

In general, two techniques have been traditionally used to sequence nucleic acids. In the first method, termed "Maxam and Gilbert sequencing" after its co-developers (Maxam, A. M. and Gilbert, W., *Proc. Natl. Acad. Sci. USA* 74:560-564, 1977), DNA is radiolabeled, divided into four samples and treated with chemicals that selectively destroy specific nucleotides bases in the DNA and cleave the molecule at the sites of damage. By separating the resultant fragments into discrete bands by gel electrophoresis and exposing the gel to X-ray film, the sequence of the original DNA molecule can be read from the film. This technique has been used to determine the sequences of certain complex DNA molecules, including the primate virus SV40 (Fiers, W., et al., *Nature* 273:113-120, 1978; Reddy, V. B., et al., *Science* 200:494-502, 1978) and the bacterial plasmid pBR322 (Sutcliffe, G., *Cold Spring Harbor Symp. Quant. Biol.* 43:444-448, 1975).

An alternative technique for sequencing, named "Sanger sequencing" after its developer (Sanger, F., and Coulson, A. R., *J. Mol. Biol.* 94:444,448, 1975), is more commonly employed. This method uses the DNA-synthesizing activity of DNA polymerases which, when combined with mixtures of reaction-terminating dideoxynucleoside triphosphates (Sanger, F., et al., *Proc. Natl. Acad. Sci. USA* 74:5463-5467, 1977) and a short primer (either of which may be detectably labeled), gives rise to a series of newly synthesized DNA fragments specifically terminated at one of the four dideoxy bases. These fragments are then resolved by gel electrophoresis and the sequence determined as described for Maxam and Gilbert sequencing above. By carrying out four separate reactions (once with each ddNTP), the sequences of even fairly complex DNA molecules may rapidly be determined (Sanger, F., et al., *Nature* 265:678-695, 1977; Barnes, W., *Meth. Enzymol.* 152:538-556, 1987). While Sanger sequencing usually employs *E. coli* or T7 DNA polymerase (U.S. Pat. No. 4,795,699), recent modifications of this technique using T7 polymerase mutants allow sequencing to be accomplished using a single sequencing reaction containing all four chain-terminating ddNTPs at different concentrations (U.S. Pat. Nos. 4,962,020 and 5,173,411). Further modifications to the technique, to reduce or eliminate the buildup of reaction-poisoning pyrophosphate in the reaction mixtures, have also been described (U.S. Pat. No. 5,498,523). Other variations for sequencing nucleic acid molecules have also been described (see Murray, *Nucl. Acids. Res.* 17:8889, 1989; and Craxton, *Methods: A Comparison to Methods in Enzymology,* 3:20-25, 1991).

Limitations

As noted above, the faithful and high-fidelity copying of a template nucleic acid molecule is an essential step in the synthesis of a nucleic acid molecule in amplification, reverse transcription, and sequencing protocols. However, the use of standard compositions and protocols to accomplish this synthesis is often inefficient, in that they tend to terminate nucleic acid synthesis prematurely at certain secondary structural (Gerard, G. F., et al., *FOCUS* 11(4):60 (1989); Myers, T. W., and Gelfand, D. H., *Biochemistry* 30:7661 (1991)) and sequence (Messer, L. I., et al., *Virol.* 146:146 (1985)); Abbotts, J., et al., *J. Biol. Chem.* 268:10312-10323 (1993)) barriers in nucleic acid templates. This is particularly true for template sequences that have high guanine/cytosine content (i.e., "GC-rich" templates) and those that are fairly large in size (i.e., templates that are larger than about 3-5 kb in length). These secondary structural and sequence barriers in the template nucleic acid molecules occur frequently at homopolymer stretches (Messer, L. I., et al., *Virol.* 146:146 (1985); Huber, H. E., et al., *J. Biol. Chem.* 264:4669-4678 (1989); Myers, T. W., and Gelfand, D. H., *Biochemistry* 30:7661 (1991)) and are more often sequence rather than secondary structural barriers (Abbotts, J., et al., *J. Biol. Chem.* 268:10312-10323 (1993)). If these barriers could be overcome, yield of total and full-length nucleic acid products in synthesis reactions could be increased.

Some reports have indicated that modulation of the ionic strength or osmolality of the reaction mixtures, particularly of the concentration of $Na^+$ and $K^+$ ions, may influence the secondary structure and condensation of nucleic acids in vitro much as they do in vivo (Le Rudulier, D., et al., *Science* 224:1064 (1984); Buche, A., et al., *J. Biomolec. Struct. Dyn.* 8(3):601 (1990); Marquet, R., and Houssier, C., *J. Biomolec.*

Struct. Dyn. 9(1):159 (1991); Buche, A., et al., *J. Biomolec. Struct. Dyn.* 11(1):95 (1993); Woodford, K., et al., *Nucl. Acids Res.* 23(3):539 (1995); Flock, S., et al., *Biophys. J.* 70:1456 (1996); Flock, S., et al., *Biophys. J.* 71:1519 (1996); EP 0 821 059 A2). In some of these studies, in vitro nucleic acid conformation and stability was found to be improved in buffer solutions containing any of a number of natural and synthetic osmoprotectant compounds, including polysaccharides such as trehalose (Carninci, P., et al., *Proc. Natl. Acad. Sci. USA* 95:520-524 (1998)), certain co-solvents such as glycerol and dimethylsulfoxide (Varadaraj, K., and Skinner, D. M., *Gene* 140:1 (1994)); glycine and derivatives thereof (Buche, A., et al., *FEBS Lett.* 247(2):367 (1989); Flock, S., et al., *J. Biomolec. Struct. Dyn.* 13(1):87 (1995); Houssier, C., et al., *Comp. Biochem. Physiol.* 117A(3):313 (1997)); low molecular weight amines such as beta-alanine, asparagine and cystamine (Kondakova, N. V., et al., *Mol. Biol. (Moscow)* 9(5):742 (1975); Aslanian, V. M., et al., *Biofizika* 29(4):564 (1984)); and other nitrogen-containing compounds and amino acids such as proline, betaine and ectoine (Rees, W. A., et al., *Biochemistry* 32:137-144 (1993); WO 95/20682; DE 44 11 588 C1; DE 44 11 594 C1; Mytelka, D. S., et al., *Nucl. Acids Res.* 24(14):2774 (1996); Baskaran, N., et al., *Genome Res.* 6:633 (1996); Weissensteiner, T., and Lanchbury, J. S., *BioTechniques* 21(6):1102 (1996); Rajendrakumar, C. S. V., et al, *FEBS Letts.* 410:201-205 (1997); Henke, W., et al., *Nucl. Acids Res.* 25(19):3957 (1997); Hengen, P. N., *TIBS* 22:225 (1997)). Betaine and ectoine are natural osmoprotectants in a variety of bacterial and animal cells (Chambers, S. T., et al., *J. Bacteriol.* 169(10):4845 (1987); Randall, K., et al., *Biochim. Biophys. Acta* 1291(3): 189 (1996); Randall, K., et al., *Biochem. Cell Biol.* 74(2): 283 (1996); Malin, G., and Lapidot, A., *J. Bacteriol.* 178 (2):385 (1996); Gouesbet, G., et al., *J. Bacteriol.* 178(2):447 (1996); Cánovas, D., et al., *J. Bacteriol.* 178(24):7221 (1996); Cánovas, D., et al., *J. Biol. Chem.* 272(41):25794-25801 (1997).

There remains a need in the art, however, for compounds, compositions and methods that are useful in enhancing synthesis of nucleic acid molecules, particularly those that are GC-rich and/or those that are relatively large.

BRIEF SUMMARY OF THE INVENTION

The present invention relates generally to compounds, compositions and methods useful in enhancing synthesis of nucleic acid molecules, especially from GC-rich nucleic acid templates. In one aspect, the invention relates to compounds and compositions for use in synthesizing a nucleic acid molecule, particularly for template mediated synthesis such as in amplification, reverse transcription, and sequencing reactions. The compounds and compositions of the invention comprise one or more compounds having a chemical formula selected from the group consisting of formula I and formula II, and salts and derivatives thereof. In a preferred aspect, the compounds used in the invention include any amino acid, any saccharide (monosaccharide or polysaccharide), any polyalcohol, or salts or derivatives thereof. The compounds or compositions of the invention include compounds having the chemical formula as set forth in formula I or formula II, or salts or derivatives thereof, wherein the aryl group is selected from the group consisting of phenyl, naphthyl, phenanthryl, anthracyl, indenyl, azulenyl, biphenyl, biphenylenyl and fluorenyl groups; wherein the halo group is selected from the group consisting of fluorine, chlorine, bromine and iodine; wherein the alkyl group is selected from the group consisting of methyl, ethyl, propyl, isopropyl, butyl, pentyl, hexyl, heptyl, octyl, nonyl, and decyl, and may be a branched chain alkyl group; wherein the alkenyl group is selected from the group consisting of ethenyl, propenyl, butenyl, pentenyl, hexenyl, heptenyl, octenyl, nonenyl and decenyl, and may be a branched chain alkenyl group; wherein the alkynyl group is selected from the group consisting of ethynyl, propynyl, butynyl, pentynyl, hexynyl, heptynyl, octynyl, nonynyl and decynyl, and may be a branched chain alkynyl group; and wherein the lower alkoxy (ether) group is oxygen substituted by one of the alkyl groups mentioned above. The invention also relates to salts and derivatives of such compounds. In particularly preferred aspect of the invention, the compounds are selected from the group consisting of 4-methylmorpholine N-oxide, betaine, carnitine, ectoine, proline, glycine, pipecolic acid, trimethylamine N-oxide, N-alkylimidazole compounds such as 1-methylimidazole or 4-methylimidazole, poly(2-ethyl-2-oxazoline) of average molecular weight about 50,000 to about 500,000 daltons, poly(diallyldimethylammonium chloride) of average molecular weight about 100,000 to about 200,000 daltons, or salts or derivatives thereof. The invention also relates to compositions which comprise the compounds of the invention and one or more additional components selected from the group consisting of (i) one or more enzymes having nucleic acid polymerase activity, which may be thermostable enzymes, (ii) one or more nucleotides, (iii) one or more buffering salts, and (iv) one or more nucleic acid molecules. Preferred such enzymes according to this aspect of the invention may include a DNA polymerase (such as Taq, Tne, Tma, Pfu, VENT™, DEEPVENT™ and Tth DNA polymerases, and mutants, variants and derivatives thereof), an RNA polymerase (such as SP6, T7 or T3 RNA polymerase and mutants, variants and derivatives thereof) and a reverse transcriptase (such as M-MLV reverse transcriptase, RSV reverse transcriptase, AMV reverse transcriptase, RAV reverse transcriptase, MAV reverse transcriptase and HIV reverse transcriptase and mutants, variants and derivatives thereof). Preferably such reverse transcriptases are reduced or substantially reduced in RNase H activity.

The invention also relates to methods for synthesizing a nucleic acid molecule, comprising (a) mixing a nucleic acid template (which may be a DNA molecule such as a cDNA molecule, or an RNA molecule such as a mRNA molecule) with one or more (preferably two or more, three or more, four or more, five or more etc.) of the compounds or compositions of the invention to form a mixture; and (b) incubating the mixture under conditions sufficient to make a first nucleic acid molecule complementary to all or a portion of the template. Such methods of the invention may optionally comprise one or more additional steps, such as incubating the above-described first nucleic acid molecule under conditions sufficient to make a second nucleic acid molecule complementary to all or a portion of the first nucleic acid molecule. The invention also relates to nucleic acid molecules made by these methods, to vectors (which may be expression vectors) comprising these nucleic acid molecules, and to host cells comprising these nucleic acid molecules or vectors. The invention also relates to methods of producing a polypeptide, comprising culturing the above-described host cells under conditions favoring the production of the polypeptide by the host cells, and isolating the polypeptide. The invention also relates to polypeptides produced by such methods.

The invention also relates to methods for amplifying a nucleic acid molecule comprising (a) mixing a nucleic acid template with one or more of the compounds or compositions of the invention to form a mixture; and (b) incubating the mixture under conditions sufficient to amplify a nucleic acid molecule complementary to all or a portion of the template. More specifically, the invention relates to a method of amplifying a DNA molecule comprising:

(a) providing a first and second primer, wherein said first primer is complementary to a sequence at or near the 3'-termini of the first strand of said DNA molecule and said second primer is complementary to a sequence at or near the 3'-termini of the second strand of said DNA molecule;

(b) hybridizing said first primer to said first strand and said second primer to said second strand in the presence of one or more compounds or compositions of the invention, under conditions such that a third DNA molecule complementary to said first strand and a fourth DNA molecule complementary to said second strand are synthesized;

(c) denaturing said first and third strand, and said second and fourth strands; and (d) repeating steps (a) to (c) one or more times.

Such conditions may include incubation in the presence of one or more polymerases, one or more nucleotides and/or one or more buffering salts. The invention also relates to nucleic acid molecules amplified by these methods.

The invention also relates to methods for sequencing a nucleic acid molecule comprising (a) mixing a nucleic acid molecule to be sequenced with one or more primers, one or more of the compounds or compositions of the invention, one or more nucleotides and one or more terminating agents to form a mixture; (b) incubating the mixture under conditions sufficient to synthesize a population of molecules complementary to all or a portion of the molecule to be sequenced; and (c) separating the population to determine the nucleotide sequence of all or a portion of the molecule to be sequenced. The invention more specifically relates to a method of sequencing a DNA molecule, comprising:

(a) hybridizing a primer to a first DNA molecule;

(b) contacting said molecule of step (a) with deoxyribonucleoside triphosphates, one or more compounds or compositions of the invention, and one or more terminator nucleotides;

(c) incubating the mixture of step (b) under conditions sufficient to synthesize a random population of DNA molecules complementary to said first DNA molecule, wherein said synthesized DNA molecules are shorter in length than said first DNA molecule and wherein said synthesized DNA molecules comprise a terminator nucleotide at their 3' termini; and (d) separating said synthesized DNA molecules by size so that at least a part of the nucleotide sequence of said first DNA molecule can be determined.

Such terminator nucleotides include ddNTP, ddATP, ddGTP, ddITP or ddCTP. Such conditions may include incubation in the presence of one or more DNA polymerases and/or buffering salts.

The invention also relates to kits for use in synthesis of a nucleic acid molecule, comprising one or more containers containing one or more of the compounds or compositions of the invention. These kits of the invention may optionally comprise one or more additional components selected from the group consisting of one or more nucleotides, one or more polymerases and/or reverse transcriptases, a suitable buffer, one or more primers and one or more terminating agents (such as one or more dideoxynucleotides).

Other preferred embodiments of the present invention will be apparent to one of ordinary skill in light of the following drawings and description of the invention, and of the claims.

DETAILED DESCRIPTION OF THE INVENTION

Definitions

Figure 1:
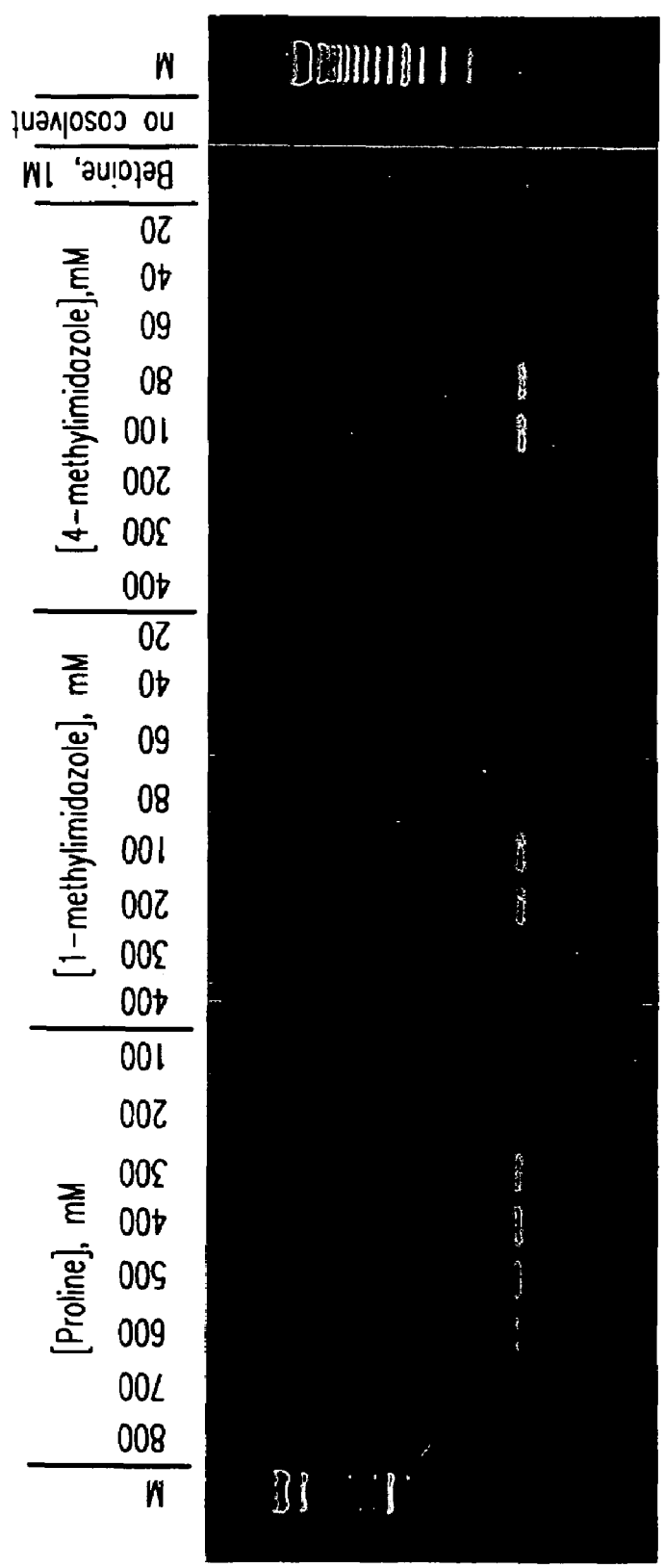
FIG. 1 is a photograph of an ethidium bromide-stained agarose gel of samples of PCR reaction mixtures amplified in the presence of the indicated concentrations of proline, 1-methylimidazole, 4-methylimidazole, betaine, or none of these cosolvents. M: DNA sizing markers.

In the description that follows, a number of terms used in recombinant DNA technology are utilized extensively. In order to provide a clearer and consistent understanding of the specification and claims, including the scope to be given such terms, the following definitions are provided.

Library. As used herein, the term "library" or "nucleic acid library" means a set of nucleic acid molecules (circular or linear) representative of all or a significant portion of the DNA content of an organism (a "genomic library"), or a set of nucleic acid molecules representative of all or a significant portion of the expressed genes (a "cDNA library") in a cell, tissue, organ or organism. Such libraries may or may not be contained in one or more vectors.

Vector. As used herein, a "vector" is a plasmid, cosmid, phagemid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector. Markers, for example, include but are not limited to tetracycline resistance or ampicillin resistance.

Primer. As used herein, "primer" refers to a single-stranded oligonucleotide that is extended by covalent bonding of nucleotide monomers during amplification or polymerization of a DNA molecule.

Template. The term "template" as used herein refers to double-stranded or single-stranded nucleic acid molecules which are to be amplified, synthesized or sequenced. In the case of a double-stranded molecules, denaturation of its strands to form a first and a second strand is preferably performed before these molecules may be amplified, synthesized or sequenced, or the double stranded molecule may be used directly as a template. For single stranded templates, a primer, complementary to a portion of the template is hybridized under appropriate conditions and one or more polymerases may then synthesize a nucleic acid molecule complementary to all or a portion of said template. Alternatively, for double stranded templates, one or more promoters (e.g. SP6, T7 or T3 promoters) may be used in combination with one or more polymerases to make nucleic acid molecules complementary to all or a portion of the template. The newly synthesized molecules, according to the invention, may be equal or shorter in length than the original template.

Incorporating. The term "incorporating" as used herein means becoming a part of a DNA and/or RNA molecule or primer.

Amplification. As used herein "amplification" refers to any in vitro method for increasing the number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reactions (PCR). One PCR reaction may consist of 5 to 100 "cycles" of denaturation and synthesis of a DNA molecule.

Oligonucleotide. "Oligonucleotide" refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization. The terms "hybridization" and "hybridizing" refers to base pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

Unit. The term "unit" as used herein refers to the activity of an enzyme. When referring, for example, to a thermostable DNA polymerase, one unit of activity is the amount of enzyme that will incorporate 10 nanomoles of dNTPs into acid-insoluble material (i.e., DNA or RNA) in 30 minutes under standard primed DNA synthesis conditions.

Other terms used in the fields of recombinant DNA technology and molecular and cell biology as used herein will be generally understood by one of ordinary skill in the applicable arts.

Overview

The present invention relates generally to compounds, compositions and methods useful in enhancing synthesis of nucleic acid molecules, especially GC-rich nucleic acid templates. Specifically, the invention provides compounds and compositions comprising one or more compounds having a formula selected from the group consisting of formula I and formula II, or salts or derivatives thereof. Preferably, at least two, at least three, at least four, at least five, at least six, etc. of such compounds or compositions are used in accordance with the invention. Most preferably, 2 to 6, 2 to 5, 2 to 4 or 2 to 3 of such compounds or compositions are used. The compounds or compositions of the invention may be in the form of a salt.

Formula I:

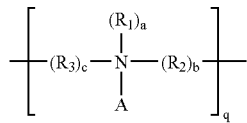

wherein A is

wherein X is

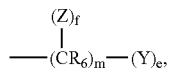

wherein Z may be the same as or different from Y, wherein each Y and Z are independently selected from the group consisting of —OH, —NH$_2$, —SH, —PO$_3$H, —CO$_2$H, —SO$_3$H and hydrogen; f is an integer from 0 to 2, m is an integer from 0 to 20 and e is an integer from 0 to 2;

wherein R$_4$, R$_5$ and R$_6$ may be the same or different and are independently selected from the group consisting of hydrogen, alkyl, alkenyl, alkynyl, aryl, amino, thiol, mercaptan, halo, nitro, nitrilo, hydroxy, hydroxyalkyl, hydroxyaryl, phosphato, alkoxy, oxide, ether, ester (alkanoyloxy), carboxy carbonyl, sulfonyl, sulfonic and amido groups, and d is an integer from 0 to 2;

wherein a, b, and c are independently an integer from 0 to 1, with the proviso that no more than two of a, b, and c are zero;

wherein R$_1$, R$_2$ and R$_3$ may be the same or different and are independently selected from the group consisting of:

a) 

b) 

wherein each R$_7$ and W may be the same or different and are independently selected from the group consisting of hydrogen, alkyl, alkenyl, alkynyl, aryl, amino, thiol, mercaptan, halo, nitro, nitrilo, hydroxy, hydroxyalkyl, hydroxyaryl, phosphato, alkoxy, oxide, ether, ester (alkanoyloxy), carboxy, carbonyl, sulfonyl, sulfonic, and amido groups; g is an integer from 0 to 2, and n is an integer from 0 to 20; and wherein q may be 1 to 100,000.

In compounds of formula I, when q=1, the compound of formula I may be considered a monomer, and when q=2 to 100,000, the compound of formula I may be considered a multimer or a polymer composed of 2 to 100,000 monomers, which may each have the same or different structures, and which may be connected by one or more bonds through one or more groups to form a multimer (e.g., a polymer) of the compound of formula I.

In a preferred aspect, when a, b, or c is zero, the corresponding R group is a pair of electrons.

In another preferred embodiment, when q=1 and one of (R$_1$)$_a$, (R$_2$)$_b$, and (R$_3$)$_c$ is =O and the other two R groups are the same or different and are independently selected from the group consisting of hydrogen, methyl, ethyl and propyl, then A is not methyl, ethyl, or propyl.

Formula II:

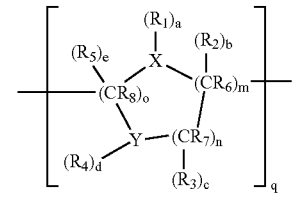

wherein Formula II is saturated or unsaturated;

wherein q may be 1 to 100,000;

wherein X is selected from the group consisting of N, C, O, P and S;

wherein Y is selected from the group consisting of O, N, S, P, C, —O—NH—, —O—CH$_2$—O—, —O—S—, —O—CH$_2$—S—, —O—CH$_2$—NH—, —NH—S—, —NH—CH$_2$—NH—, —O—CH(CH$_3$)—NH—, —NH—CH(CH$_3$)—NH—, —O—CH(CH$_3$)—O—, —NH—C(CH$_3$)$_2$—NH—, —NH—CH$_2$—S—, and other mercaptan, phosphato, alkoxy, oxide, ether, ester (alkanoyloxy), carboxy, sulfonyl, sulfonic and amido groups;

wherein R$_1$, R$_2$, R$_3$, R$_4$, R$_5$, R$_6$, R$_7$ and R$_8$ may be the same or different and are independently selected from the group consisting of hydrogen, alkyl, alkenyl, alkynyl, aryl, amino, thiol, mercaptan, halo, nitro, nitrilo, hydroxy, hydroxyalkyl, hydroxyaryl, phosphato, alkoxy, oxide, ether, ester (alkanoyloxy), carboxy, sulfonyl, sulfonic and amido groups; and wherein a, b, c, d, e, m, n, and o are integers which may be the same or different and are independently selected from 0 to 2 for a, b, c, d and e, and 0 to 5 for m, n, and o.

In compounds of formula II, when q=1, the compound of formula II may be considered a monomer, and when q=2 to 100,000, the compound of formula II may be considered a multimer or a polymer composed of 2 to 100,000 monomers, which may each have the same or different structures, and which may be connected by one or more bonds through one or more groups to form a multimer (e.g., a polymer) of the compound of formula II.

In one preferred aspect of the invention, Y and/or X are N, and m, n, and o are 1. In another preferred aspect, Y and/or X are N and/or O, and m and n are 1, and o is 2. Preferably, when a, b, c, d and/or e are zero, the corresponding R group is a pair of electrons or involved in the formation of the unsaturated structures.

For compounds of formulae I and II:
typical $C_{6-14}$ aryl groups include, but are not limited to, phenyl, benzyl, methylindolyl, naphthyl, phenanthryl, anthracyl, indenyl, azulenyl, biphenyl, biphenylenyl and fluorenyl groups;
typical halo groups include, but are not limited to, fluorine, chlorine, bromine and iodine;
typical $C_{1-15}$ alkyl groups include, but are not limited to, methyl, ethyl, propyl, isopropyl, butyl, pentyl, hexyl, heptyl, octyl, nonyl, decyl groups as well as branched chain alkyl groups;
typical $C_{2-15}$ alkenyl groups include, but are not limited to, ethenyl, propenyl, butenyl, pentenyl, hexenyl, heptenyl, octenyl, nonenyl, decenyl groups and the like as well as the branched chain alkenyl groups;
typical $C_{2-15}$ alkynyl groups include ethynyl, propynyl, butynyl, pentynyl, hexynyl, heptynyl, octynyl, nonynyl, decynyl groups and the like as well as the branched chain alkynyl groups;
typical lower alkoxy (ether) groups include oxygen substituted by one of the $C_{1-4}$ alkyl groups mentioned above; and
typical $C_{2-6}$ alkanoyloxy groups include acetoxy, propionyloxy, butanoyloxy, pentanoyloxy, hexanoyloxy and branched chain isomers thereof.

Compounds which may be used in accordance with the invention include saccharides, amino acids, and polyalcohols, and derivatives thereof. Examples of saccharides include but are not limited to oligosaccharides and monosaccharides such as trehalose, maltose, glucose, sucrose, lactose, xylobiose, agarobiose, cellobiose, levanbiose, quitobiose, 2-β-glucuronosylglucuronic acid, allose, altrose, galactose, gulose, idose, mannose, talose, sorbitol, levulose, xylitol and arabitol.

Such amino acids may include but are not limited to alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, and histidine, and derivatives thereof. Both the D and L forms of the amino acids, and non-protein amino acids, may be used in accordance with the invention. Examples include N-(3'-one-5'-methyl)-hexylalanine, leucine betaine, N-methylisoleucine, and γ-glutamyl leucine.

Examples of polyalcohols include but are not limited to glycerol, ethylene glycol, polyethylene glycol and the like.

Preferred compounds of the invention may include, but are not limited to, 4-methylmorpholine N-oxide (MMNO), and N-alkylimidazole compounds such as 1-methylimidazole, 2-methylimidazole, and 4-methylimidazole, betaine (carboxymethyl-trimethylammonium), taurine, ectoine, pipecolinic acid, pipecolic acid, 2-morpholinoethanesulfonic acid, pyridine N-oxide, N,N-dimethyloctylamine N-oxide, 3-methylisoxazol-5(4H)-one morpholine salt, glycine, sorcosine, N-N-dimethyl glycine, N-methyl-proline, 4-hydroxy-proline, 1-methyl-2-pyrrolecarboxylic acid, 1-methylindole-2-carboxylic acid, 2-pyrazinecarboxylic acid, 5-methyl-2-pyrazinecarboxylic acid, 4-methyl-5-imidazole-carboxoaldehyde, 1-methylpyrrole-2-carboxylic acid, 1-ethyl-3-methylimidazolium nitrate, ethyl azetidine-l-propionate, N,N-dimethyl-phenylalanine, S-carboxymethyl-cysteine, 2-imidazolecarboxaldehyde,4-imidazoleacetic acid, 4-imidazole carboxylic acid, 4,5-imidazdedicarboxylic acid, carnitine $N^e$-acetyl-b-lysine, γ-aminobutyric acid, trans-4-hydroxystachydrine, Nα-carbamoyl-L-glutamine 1-amide, choline, dimethylthetine, (sulfobetaine and dimethylacetothetin, and derivatives thereof), N-acetylglutaminylglutamine amide, dimethylsulfoniopropionate, ectoine (1,4,5,6-tetrahydro-2methyl-4-pirymidine carboxilic acid), hydroxyectoine, glutamate, β-glutammine, octopine, sarcosine, and trymethylamine N-oxide (TMAO), poly(2-ethyl-2-oxazoline) of average molecular weight about 50,000 to about 500,000 daltons, poly(diallyldimethylammonium chloride) of average molecular weight about 100,000 to about 200,000 daltons, and all other amino acids and derivatives thereof.

Additional preferred compounds include derivatives and salts of the compounds of formulae I and II. For example, when the compound of formula I or formula II contains a carboxyl (C=O) group, the compounds of the invention include esters and amides of the carboxyl group which may be prepared using routine methods of chemical synthesis, for example by condensing the carboxyl-containing compound with an alcohol or amino compound. Examples of alcohols useful according to this aspect of the invention include $C_{1-6}$ alcohols and $C_{7-12}$ aralkanol compounds, including but not limited to methanol, ethanol, propanol, butanol, pentanol, hexanol, and branched chain isomers thereof. Examples of amino compounds useful according to this aspect of the invention include $C_{1-6}$ amino compounds and $C_{7-12}$ aralkamino compounds, including but not limited to methylamine, ethylamine, propylamine, butylamine, pentylamine, hexylamine, and branched chain isomers thereof. When the compound of formula I or formula II contains a hydroxy (—OH) group, the compounds of the invention include the esters of such compounds which may be prepared by condensing the hydroxy-containing compound with, for example, a $C_{1-6}$ alkanoic acid, a $C_{6-12}$ aralkanoic acid, or $C_{2,12}$ dialkanoic acid or an anhydride thereof, e.g., formic acid, acetic acid, propionic acid, butyric acid, pentanoic acid, hexanoic acid, and branched chain isomers thereof, as well as succinic acid, succinic anhydride, fumaric acid, maleic acid, and the like. Other derivatives of the compounds of formulae I and II that may be prepared and used in accordance with the present invention will be apparent to one of ordinary skill in view of the teachings contained herein and knowledge in the art.

Also included within the scope of the present invention are the salts of the compounds of formulae I and II. Acid addition salts of the compounds of formulae I and II may be formed by routine methods of chemical synthesis, for example by mixing a solution of the particular compound with a solution of an acid, such as hydrochloric acid, fumaric acid, maleic acid, succinic acid, acetic acid, citric acid, tartaric acid, carbonic acid, phosphoric acid, oxalic acid, and the like. Basic salts of the compounds of formulae I and II may be formed using routine methods of chemical synthesis, for example by mixing a solution of the particular compound with a solution of a base, such as sodium hydroxide, potassium hydroxide, choline hydroxide, sodium carbonate, Tris, and the like. Other salts of the compounds of formulae I and II that may be prepared and used in accordance with the present invention will be apparent to one of ordinary skill in view of the teachings contained herein and knowledge in the art.

The above mentioned compounds and compositions may be used alone or in any combination thereof. Preferably, combinations of at least two, at least three, at least four, at least five, etc. are used in accordance with the invention. In a preferred aspect, 2 to 10, 2 to 9, 2 to 8, 2 to 7, 2 to 6, 2 to 5, 2 to 4, and 2 to 3 of such compounds are used. In a preferred aspect, the invention relates to the compositions obtained by mixing any combination of the above mentioned compounds. In mixing such compounds together, certain interactions may take place which may change the structure of one or more of the compounds being mixed and result in the formation of new or different compounds.

These compositions may be used in methods for enhanced, high-fidelity synthesis of nucleic acid molecules, including via amplification (particularly PCR), reverse transcription, and sequencing methods. The invention also relates to nucleic acid molecules produced by these methods, to fragments or derivatives thereof, and to vectors and host cells comprising such nucleic acid molecules, fragments, or derivatives. The invention also relates to the use of such nucleic acid molecules to produce desired polypeptides. The invention also concerns kits comprising the compounds or compositions of the invention.

Synthesis Methods

Compounds of formulae I and II may be synthesized using standard techniques of organic chemical synthesis known to one of ordinary skill, as follows.

Synthesis of compounds of formula I may be carried out as follows:

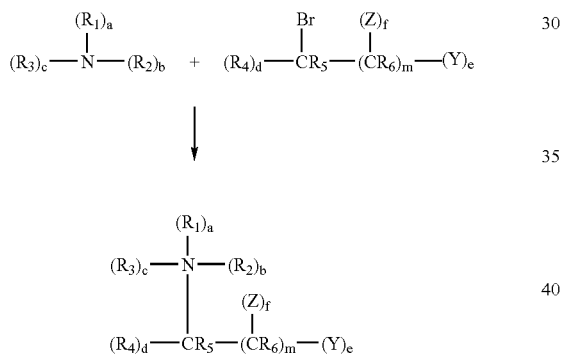

For example, when $R_4$ and Z are H, Y is $-CO_2H$, d, e, f and m are 1, then the starting chemical is $BrCH_2CH_2CO_2H$ which is commercially available.

Synthesis of compounds of Formula II may be carried out as follows:

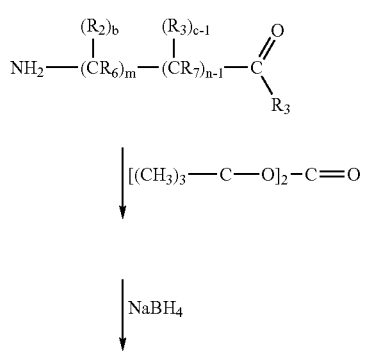

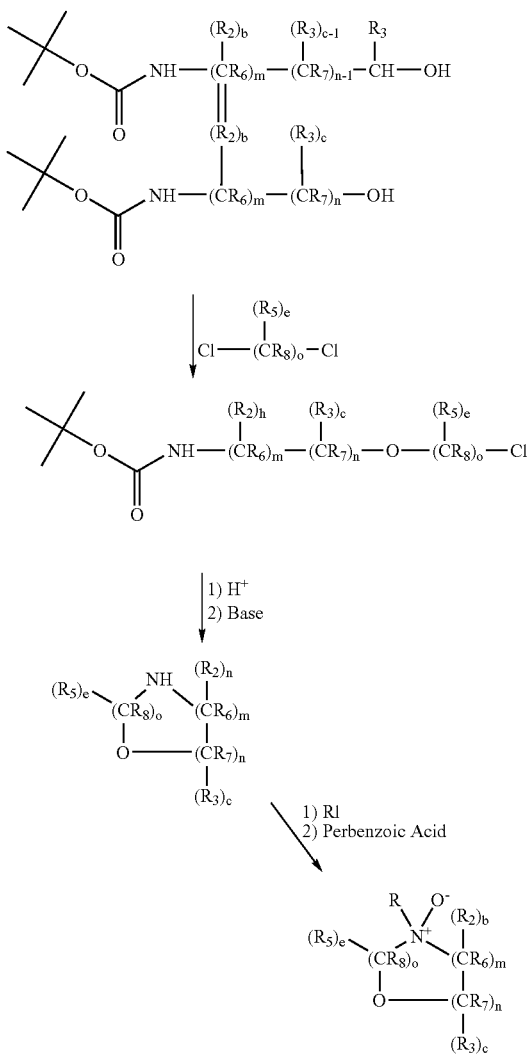

For example, when $R_2$ and $R_3$ are H; b and m are 1; c–1 and n–1 are zero, then the starting chemical is $NH_2-CH_2-COH$ which is commercially available.

Also available commercially are $BrCH_2CO_2H$, $CH_3CH(Br)CO_2H$, $CH_2-CH_2CH(Br)CO_2H$, $BrCH_2CH_2CH_2CO_2H$, $Cl-CH_2-CH_2-Cl(CH_3)_2CHCH(Br)CO_2$, $CH_3CH_2CH(Br)CO_2H$, $BrCH_2CH_2CH_2CO_2H$, $BrCH_2CH_2CO_2H$, $HO_2CCH_2CH(Br)CO_2H$. Such compounds may be obtained from Aldrich (St. Louis, Mo.).

Numerous compounds for use in the invention, such as amino acids and their derivatives, saccharides and their derivatives, and N-alkylimidazole compounds (including 1-methylimidazole and 4-methylimidazole) may be obtained commercially, for example from Sigma (St. Louis, Mo.).

To formulate the compositions of the invention, one or more of the above-described compounds may be mixed together in any manner. Such mixtures may be accomplished by admixing these compounds in their powdered form, preparing a solution of each compound in an aqueous or organic solvent and admixing the solutions to form the compositions of the invention, or preparing a solution of at least one compound and admixing the powdered form of one or more additional compounds.

In an additional preferred aspect of the invention, the present compositions may further comprise one or more polypeptides having nucleic acid polymerase activity. Preferred such enzymes having nucleic acid polymerase activity may include, but are not limited to, polypeptides having DNA polymerase activity, polypeptides having RNA polymerase activity, and polypeptides having reverse transcriptase activity.

More preferably, the present compositions are provided at working concentrations or as concentrates (2×, 5×, 10×, 50× etc.). Such compositions are preferably stable upon storage at various temperatures. The terms "stable" and "stability" as used herein generally mean the retention by a component, such as a compound or an enzyme of the composition, of at least 70%, preferably at least 80%, and most preferably at least 90%, of the original enzyme and/or compound activity after the composition has been stored for about one week at a temperature of about 4° C., about six months at a temperature of about −20° C. As used herein, the term "working concentration" means the concentration of a chemical compound or an enzyme that is at or near the optimal concentration used in a solution to perform a particular function (such as synthesis of nucleic acids).

Water which may be used in forming the compositions of the present invention is preferably distilled, deionized and sterile filtered (through a 0.1-0.2 micrometer filter), and is free of contamination by DNase and RNase enzymes. Such water is available commercially, for example from Sigma Chemical Company (St. Louis, Mo.), or may be made as needed according to methods well known to those skilled in the art.

In addition to the chemical (and optionally polypeptide) components, the present compositions preferably comprise one or more buffers and cofactors necessary for synthesis of a nucleic acid molecule. Particularly preferred buffers for use in forming the present compositions are the acetate, sulfate, hydrochloride, phosphate or free acid forms of Tris-(hydroxymethyl)aminomethane (TRIS®), although alternative buffers of the same approximate ionic strength and pKa as TRIS® may be used with equivalent results. In addition to the buffer salts, cofactor salts such as those of potassium (preferably potassium chloride or potassium acetate) and magnesium (preferably magnesium chloride or magnesium acetate) are included in the compositions.

It is often preferable to first dissolve the buffer and cofactor salts at working concentrations in water and to adjust the pH of the solution prior to addition of the chemical compounds (and optionally the polypeptides). In this way, any pH-sensitive chemical compounds and polypeptides will be less subject to acid- or alkaline-mediated inactivation or degradation during formulation of the present compositions.

To formulate the buffered salts solution, a buffer salt which is preferably a salt of Tris(hydroxymethyl)aminomethane (TRIS®), and most preferably the hydrochloride salt thereof, is combined with a sufficient quantity of water to yield a solution having a TRIS® concentration of 5-150 millimolar, preferably 10-60 millimolar, and most preferably about 20-60 millimolar. To this solution, a salt of magnesium (preferably either the chloride or acetate salt thereof) may be added to provide a working concentration thereof of 1-10 millimolar, preferably 1.5-8.0 millimolar, and most preferably about 3-7.5 millimolar. A salt of potassium (most preferably potassium chloride) may also be added to the solution, at a working concentration of 10-100 millimolar and most preferably about 75 millimolar. A reducing agent such as dithiothreitol may be added to the solution, preferably at a final concentration of about 1-100 mM, more preferably a concentration of about 5-50 mM or about 7.5-20 mM, and most preferably at a concentration of about 10 mM. A small amount of a salt of ethylenediaminetetraacetate (EDTA), such as disodium EDTA, may also be added (preferably about 0.1 millimolar), although inclusion of EDTA does not appear to be essential to the function or stability of the compositions of the present invention. After addition of all buffers and salts, this buffered salt solution is mixed well until all salts are dissolved, and the pH is adjusted using methods known in the art to a pH value of 7.4 to 9.2, preferably 8.0 to 9.0, and most preferably about 8.4.

To these buffered salt solutions, compounds of the invention, and optionally the one or more polypeptides having nucleic acid polymerase activity, are added to produce the present compositions.

In preferred compositions, the compounds of the invention are mixed at a molar or stoichiometric ratio of about 10:1, about 9:1, about 8:1, about 7:1, about 6:1, about 5:1, about 4:1, about 3:1, about 2.5:1, about 2:1, about 1.75:1, about 1.5:1, about 1.25:1, about 1:1, about 1:1.25, about 1:1.5, about 1:1.75, about 1:2, about 1:2.5, about 1:3, about 1:4, about 1:5, about 1:6, about 1:7, about 1:8, about 1:9, or about 1:10. More preferably, the compounds are mixed at a molar or stoichiometric ratio of about 1:1. Other molar or stoichiometric ratios may be determined by routine optimization. If more than two compounds are used to form the compositions of the invention, of the amount of each compound may easily be optimized by examining the effect on nucleic acid synthesis. These compounds are then preferably formulated into the compositions at working concentrations, for use in the nucleic acid synthesis methods described below, of about 0.01-5 M, about 0.05-5 M, about 0.1-4 M, about 0.25-3 M, about 0.3-2.5 M, about 0.4-2 M, about 0.4-1.5 M, about 0.4-1 M, or about 0.4-0.8 M. Depending on the compounds used, other molar amounts may be used depending on the desired result. The compositions of the invention may then be stored at two to four weeks at 65° C., one to two months at room temperature to 37° C., one to six months at 4° C. and three months to a year or longer at −20° C., until use in the synthesis of nucleic acid molecules.

A variety of polypeptides having polymerase activity are useful in accordance with the present invention. Included among these polypeptides are enzymes such as nucleic acid polymerases (including DNA polymerases and RNA polymerases). Such polymerases include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Pyrococcus* sp KDD2 (KOD) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, variants and derivatives thereof. RNA polymerases such as T3, T5 and SP6 and mutants, variants and derivatives thereof may also be used in accordance with the invention.

The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods and compositions of the invention include Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29-35 (1992); Lawyer, F. C., et al., *PCR Meth. Appl.* 2:275-287 (1993); Flaman, J.-M, et al., *Nucl. Acids Res.* 22(15):3259-3260 (1994)). For amplification of long nucleic acid molecules (e.g., nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Barnes, W. M., *Gene* 112:29-35 (1992); and copending U.S. patent application Ser. No. 08/801,720, filed Feb. 14, 1997, the disclosures of which are incorporated herein in their entireties. Examples of DNA polymerases substantially lacking in 3' exonuclease activity include, but are not limited to, Taq, Tne(exo⁻), Tma(exo⁻), Pfu (exo⁻), Pwo(exo⁻) and Tth DNA polymerases, and mutants, variants and derivatives thereof.

Polypeptides having reverse transcriptase activity for use in the invention include any polypeptide having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487-491 (1988); U.S. Pat. Nos. 4,889,818 and 4,965,188), Tne DNA polymerase (WO 96/10640), Tma DNA polymerase (U. S. Pat. No. 5,374,553) and mutants, variants or derivatives thereof (see, e.g., copending U.S. patent application Ser. Nos. 08/706,702 and 08/706,706, of A. John Hughes and Deb K. Chatterjee, both filed Sep. 9, 1996, which are incorporated by reference herein in their entireties). Preferred enzymes for use in the invention include those that are reduced or substantially reduced in RNase H activity. By an enzyme "substantially reduced in RNase H activity" is meant that the enzyme has less than about 20%, more preferably less than about 15%, 10% or 5%, and most preferably less than about 2%, of the RNase H activity of the corresponding wildtype or RNase H⁺ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988) and in Gerard, G. F., et al., *FOCUS* 14(5):91 (1992), the disclosures of all of which are fully incorporated herein by reference. Particularly preferred such polypeptides for use in the invention include, but are not limited to, M-MLV H⁻ reverse transcriptase, RSV H⁻ reverse transcriptase, AMV H⁻ reverse transcriptase, RAV (Rous-associated virus) H⁻ reverse transcriptase, MAV (myeloblastosis-associated virus) H⁻ reverse transcriptase and HIV H⁻ reverse transcriptase. It will be understood by one of ordinary skill, however, that any enzyme capable of producing a DNA molecule from a ribonucleic acid molecule (i.e., having reverse transcriptase activity) that is substantially reduced in RNase H activity may be equivalently used in the compositions, methods and kits of the invention.

DNA and RNA polymerases for use in the invention may be obtained commercially, for example from Invitrogen Corp. (Carlsbad, Calif.), Perkin-Elmer (Branchburg, N.J.), New England BioLabs (Beverly, Mass.) or Boehringer Mannheim Biochemicals (Indianapolis, Ind.). Polypeptides having reverse transcriptase activity for use in the invention may be obtained commercially, for example from Invitrogen Corp. (Carlsbad, Calif.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, the polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372-3376 (1988)).

Polypeptides having polyrnerase or reverse transcriptase activity are preferably used in the present compositions and methods at a final concentration in solution of about 0.1-200 units per milliliter, about 0.1-50 units per milliliter, about 0.1-40 units per milliliter, about 0.1-3.6 units per milliliter, about 0.1-34 units per milliliter, about 0.1-32 units per milliliter, about 0.1-30 units per milliliter, or about 0.1-20 units per milliliter, and most preferably at a concentration of about 20-40 units per milliliter. Of course, other suitable concentrations of such polymerases or reverse transcriptases suitable for use in the invention will be apparent to one or ordinary skill in the art.

Methods of Nucleic Acid Synthesis

The compounds and compositions of the invention may be used in methods for the synthesis of nucleic acids. In particular, it has been discovered that the present compounds and compositions facilitate the synthesis, particularly via amplification reactions such as the polymerase chain reaction (PCR), of nucleic acid molecules that have a high content of guanine and cytosine (i.e., "GC-rich" nucleic acid molecules). The present compounds and compositions may therefore be used in any method requiring the synthesis of nucleic acid molecules, such as DNA (particularly cDNA) and RNA (particularly mRNA) molecules. Methods in which the compounds or compositions of the invention may advantageously be used include, but are not limited to, nucleic acid synthesis methods, nucleic acid amplification methods, nucleic acid reverse transcription methods, and nucleic acid sequencing methods.

Synthesis

Nucleic acid synthesis methods according to this aspect of the invention may comprise one or more steps. For example, the invention provides a method for synthesizing a nucleic acid molecule comprising (a) mixing a nucleic acid template with one or more of the above-described compounds and compositions of the invention to form a mixture; and (b) incubating the mixture under conditions sufficient to make a first nucleic acid molecule complementary to all or a portion of the template. According to this aspect of the invention, the nucleic acid template may be a DNA molecule such as a cDNA molecule or library, or an RNA molecule such as a mRNA molecule.

In accordance with the invention, the input nucleic acid molecules or libraries may be prepared from populations of nucleic acid molecules obtained from natural sources, such as a variety of cells, tissues, organs or organisms. Cells that may be used as sources of nucleic acid molecules may be prokaryotic (bacterial cells, including those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acid molecules or libraries of nucleic acid molecules include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids or libraries for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including HIV) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, F9 cells and the like. Other cells, cell lines, tissues, organs and organisms suitable as sources of nucleic acids for use in the methods of the present invention will be apparent to one of ordinary skill in the art. These cells, tissues, organs and organisms may be obtained from their natural sources, or may be obtained commercially from sources such as American Type Culture Collection (Rockville, Md.) and others that are known to the skilled artisan.

Once the starting cells, tissues, organs or other samples are obtained, nucleic acid molecules (such as DNA, RNA (e.g., mRNA or poly A+ RNA) molecules) may be isolated, or cDNA molecules or libraries prepared therefrom, by methods that are well-known in the art (See, e.g., Maniatis, T., et al., *Cell* 15:687-701 (1978); Okayama, H., and Berg, P., *Mol. Cell. Biol.* 2:161-170 (1982); Gubler, U., and Hoffman, B. J., *Gene* 25:263-269 (1983)).

In the practice of this aspect of the invention, a first nucleic acid molecule may be synthesized by mixing a nucleic acid template obtained as described above, which is preferably a DNA molecule such as a cDNA molecule, or an RNA molecule such as an mRNA molecule or a polyA+ RNA molecule, with one or more of the above-described compounds or compositions of the invention to form a mixture. Under conditions favoring the reverse transcription (in the case of an RNA template) and/or polymerization of the input nucleic acid molecule, synthesis of a first nucleic acid molecule complementary to all or a portion of the nucleic acid template is accomplished. Such synthesis is usually accomplished in the presence of nucleotides (e.g., deoxyribonucleoside triphosphates (dNTPs), dideoxyribonucleoside triphosphates (ddNTPs) or derivatives thereof).

Alternatively, the compounds, compositions and methods of the invention may be used in single-tube synthesis of double-stranded nucleic acid molecules. In this approach, the first nucleic acid molecule synthesized as described above is incubated under conditions sufficient to make a second nucleic acid molecule complementary to all or a portion of the first nucleic acid molecule. This second strand synthesis may be accomplished, for example, by a modified Gubler-Hoffman reaction (D'Alessio, J. M., et al., *Focus* 9:1 (1987)).

Of course, other techniques of nucleic acid synthesis in which the compositions and methods of the invention may be advantageously used will be readily apparent to one of ordinary skill in the art.

Amplification and Sequencing Methods

In other aspects of the invention, the compositions of the invention may be used in methods for amplifying or sequencing nucleic acid molecules. Nucleic acid amplification methods according to this aspect of the invention may additionally comprise use of one or more polypeptides having reverse transcriptase activity, in methods generally known in the art as one-step (e.g., one-step RT-PCR) or two-step (e.g., two-step RT-PCR) reverse transcriptase-amplification reactions. For amplification of long nucleic acid molecules (i.e., greater than about 3-5 Kb in length), the compositions of the invention may comprise a combination of polypeptides having DNA polymerase activity, as described in detail in commonly owned, co-pending U.S. application Ser. No. 08/801,720, filed Feb. 14, 1997, the disclosure of which is incorporated herein by reference in its entirety.

Amplification methods according to this aspect of the invention may comprise one or more steps. For example, the invention provides a method for amplifying a nucleic acid molecule comprising (a) mixing a nucleic acid template with one or more of the above-described compounds or compositions of to form a mixture; and (b) incubating the mixture under conditions sufficient to amplify a nucleic acid molecule complementary to all or a portion of the template. The invention also provides nucleic acid molecules amplified by such methods.

General methods for amplification and analysis of nucleic acid molecules or fragments are well-known to one of ordinary skill in the art (see, e.g., U.S. Pat. Nos. 4,683,195; 4,683,202; and 4,800,159; Innis, M. A., et al., eds., *PCR Protocols: A Guide to Methods and Applications*, San Diego, Calif.: Academic Press, Inc. (1990); Griffin, H. G., and Griffin, A. M., eds., *PCR Technology: Current Innovations*, Boca Raton, Fla.: CRC Press (1994)). For example, amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No.5, 409,818; EP 0 329 822).

Typically, these amplification methods comprise contacting the nucleic acid sample with a compound or composition (such as those of the present invention) comprising one or more polypeptides having nucleic acid polymerase activity in the presence of one or more primer sequences, amplifying the nucleic acid sample to generate a collection of amplified nucleic acid fragments, preferably by PCR or equivalent automated amplification technique, and optionally separating the amplified nucleic acid fragments by size, preferably by gel electrophoresis, and analyzing the gels for the presence of nucleic acid fragments, for example by staining the gel with a nucleic acid-binding dye such as ethidium bromide.

Following amplification by the methods of the present invention, the amplified nucleic acid fragments may be isolated for further use or characterization. This step is usually accomplished by separation of the amplified nucleic acid fragments by size by any physical or biochemical means including gel electrophoresis, capillary electrophoresis, chromatography (including sizing, affinity and immunochromatography), density gradient centrifugation and immunoadsorption. Separation of nucleic acid fragments by gel electrophoresis is particularly preferred, as it provides a rapid and highly reproducible means of sensitive separation of a multitude of nucleic acid fragments, and permits direct, simultaneous comparison of the fragments in several samples of nucleic acids. One can extend this approach, in another preferred embodiment, to isolate and characterize these fragments or any nucleic acid fragment amplified by the methods of the invention. Thus, the invention is also directed to isolated nucleic acid molecules produced by the amplification or synthesis methods of the invention.

In this embodiment, one or more of the amplified nucleic acid fragments are removed from the gel which was used for identification (see above), according to standard techniques such as electroelution or physical excision. The isolated unique nucleic acid fragments may then be inserted into standard nucleotide vectors, including expression vectors, suitable for transfection or transformation of a variety of prokaryotic (bacterial) or eukaryotic (yeast, plant or animal including human and other mammalian) cells. Alternatively, nucleic acid molecules that are amplified and isolated using the compounds, compositions and methods of the present invention may be further characterized, for example by sequencing (i.e., determining the nucleotide sequence of the nucleic acid fragments), by methods described below and others that are standard in the art (see, e.g., U.S. Pat. Nos. 4,962,022 and 5,498,523, which are directed to methods of DNA sequencing).

Nucleic acid sequencing methods according to the invention may comprise one or more steps. For example, the invention provides a method for sequencing a nucleic acid molecule comprising (a) mixing a nucleic acid molecule to be sequenced with one or more primers, one or more of the above-described compounds or compositions of the invention, one or more nucleotides and one or more terminating agents (such as a dideoxynucleotide) to form a mixture; (b) incubating the mixture under conditions sufficient to synthesize a population of molecules complementary to all or a portion of the molecule to be sequenced; and (c) separating the population to determine the nucleotide sequence of all or a portion of the molecule to be sequenced.

Nucleic acid sequencing techniques which may employ the present compositions include dideoxy sequencing methods such as those disclosed in U.S. Pat. Nos. 4,962,022 and 5,498,523.

Vectors and Host Cells

The present invention also relates to vectors which comprise the isolated nucleic acid molecules of the present invention, host cells which are genetically engineered with the recombinant vectors, and methods for the production of a recombinant polypeptide using these vectors and host cells.

The vector used in the present invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression of a polypeptide encoded by the nucleic acid molecules of the invention; such expression vectors may be inducible and/or cell type-specific. Particularly preferred among such vectors are those inducible by environmental factors that are easy to manipulate, such as temperature and nutrient additives.

Expression vectors useful in the present invention include chromosomal-, episomal-and virus-derived vectors, e.g., vectors derived from bacterial plasmids or bacteriophages, and vectors derived from combinations thereof, such as cosmids and phagemids.

The DNA insert should be operatively linked to an appropriate promoter, such as the phage lambda $P_L$ promoter, the *E. coli* lac, trp and tac promoters. Other suitable promoters will be known to the skilled artisan. The gene fusion constructs will further contain sites for transcription initiation, termination and, in the transcribed region, a ribosome binding site for translation. The coding portion of the mature transcripts expressed by the constructs will preferably include a translation initiation codon at the beginning, and a termination codon (UAA, UGA or UAG) appropriately positioned at the end, of the polynucleotide to be translated.

The expression vectors will preferably include at least one selectable marker. Such markers include tetracycline or ampicillin resistance genes for culturing in *E. coli* and other bacteria.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; and pGEX, pTrxfus, pTrc99a, pET-5, pET-9, pKK223-3, pKK233-3, pDR540, pRIT5 available from Pharmacia. Other suitable vectors will be readily apparent to the skilled artisan.

Representative examples of appropriate host cells include, but are not limited to, bacterial cells such as *E. coli, Streptomyces* spp., *Erwinia* spp., *Klebsiella* spp. and *Salmonella typhimurium*. Preferred as a host cell is *E. coli*, and particularly preferred are *E. coli* strains DH10B and Stbl2, which are available commercially (Invitrogen Corp., Carlsbad, Calif.).

Peptide Production

As noted above, the methods of the present invention are suitable for production of any polypeptide of any length, via insertion of the above-described nucleic acid molecules or vectors into a host cell and expression of the nucleotide sequence encoding the polypeptide of interest by the host cell. Introduction of the nucleic acid molecules or vectors into a host cell to produce a transformed host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986). Once transformed host cells have been obtained, the cells may be cultivated under any physiologically compatible conditions of pH and temperature, in any suitable nutrient medium containing assimilable sources of carbon, nitrogen and essential minerals that support host cell growth. Recombinant polypeptide-producing cultivation conditions will vary according to the type of vector used to transform the host cells. For example, certain expression vectors comprise regulatory regions which require cell growth at certain temperatures, or addition of certain chemicals or inducing agents to the cell growth medium, to initiate the gene expression resulting in the production of the recombinant polypeptide. Thus, the term "recombinant polypeptide-producing conditions," as used herein, is not meant to be limited to any one set of cultivation conditions. Appropriate culture media and conditions for the above-described host cells and vectors are well-known in the art. Following its production in the host cells, the polypeptide of interest may be isolated by several techniques. To liberate the polypeptide of interest from the host cells, the cells are lysed or ruptured. This lysis may be accomplished by contacting the cells with a hypotonic solution, by treatment with a cell wall-disrupting enzyme such as lysozyme, by sonication, by treatment with high pressure, or by a combination of the above methods. Other methods of bacterial cell disruption and lysis that are known to one of ordinary skill may also be used.

Following disruption, the polypeptide may be separated from the cellular debris by any technique suitable for separation of particles in complex mixtures. The polypeptide may then be purified by well known isolation techniques. Suitable techniques for purification include, but are not limited to, ammonium sulfate or ethanol precipitation, acid extraction, electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography.

Kits

The present invention also provides kits for use in the synthesis, amplification, or sequencing of a nucleic acid molecule. Kits according to this aspect of the invention may comprise one or more containers, such as vials, tubes, ampules, bottles and the like, which may comprise one or more of the compositions of the invention.

The kits of the invention may comprise one or more of the following components: (i) one or more compounds or compositions of the invention, (ii) one or more polymerases or reverse transcriptases, (iii) one or more suitable buffers, (iv) one or more nucleotides, and (v) one or more primers.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Introduction 4-methylmorpholine N-oxide (hereinafter referred to as "MMNO") was tested on a number of different PCR amplicons containing high GC content (e.g. CAG repeats, Pseudomonas genomic DNA, etc.). The amplicons tested were difficult to amplify using current standard PCR reaction mixtures. To test the effectiveness of novel cosolvents on PCR performance from high GC-content amplicons, MMNO and other cosolvents were added to PCR reaction mixtures at different concentrations.

Methods

The following sections describe the preparation of the chemicals used in the examples.

Preparation of 2.2×PCR Mixture (Examples 1-3):

In Examples 1-3, A 2.2×PCR mixture was prepared containing all the components listed below except the template DNA and primers. The following table illustrates how to prepare a 2.2×PCR mixture.

| Stock Solution | Vol. Added | Final Concentration |
|---|---|---|
| 10X PCR Buffer | 1.1 ml | 2.2X |
| 50 mM $MgCl_2$ | 0.33 ml | 3.3 mM |
| 10 mM dNTPs | 0.22 ml | 0.44 mM |
| Tween 20 | 55 µl | 0.11% |
| Nonidet P-40 | 55 µl | 0.11% |
| Taq Polymerase (5 units/µl) | 44 µl | 44 units/ml |
| $dH_2O$ | | To 5 ml |

Materials for Examples 1-9: Betaine monohydrate ([Carboxymethyl]trimethyl-ammonium), L-proline, 4-methylmorpholine-4-oxide (MMNO), ectoine (THP[B]; [S]-2-Methyl-1,4,5,6-tetrahydropyrimidine-4-carboxylic acid), DL-pipecolic acid (DL-2-Piperidinecarboxylic acid), and L-carnitine ([-]-b-Hydroxy-g-[trimethylammonio]butyrate) were purchased from Sigma (St. Louis, Mo.), and prepared as 4M stock solutions in sterile distilled water and filter sterilized. PCR reagents: Platinum Taq DNA polymerase, Platinum Taq DNA polymerase High Fidelity, 10×Taq Buffer (1×=20 mM Tris-HCl (pH8.4), 50 mM KCl), 50 mM magnesium chloride, 10×Taq High Fidelity Buffer (1×=60 mM $Tris-SO_4$ (pH 8.9), 18 mM $(NH_4)_2SO_4$, 50 mM magnesium sulfate, 10 mM dNTP Mix, K562 human genomic DNA, and sterile distilled water were obtained from Life Technologies, Inc. (Rockville, Md.). Oligonucleotide primers were purchased as desalted preparations from Life Technologies, Inc. and were used without further purification.

Example 1

Titration of Proline, 1-methylimidazole and 4-methylimidazole to Improve PCR Amplification from a GC-rich Template Several chemicals were tested to see if they would improve PCR performance using a GC-rich template. In the first example, the GC-rich template P55G12 was tested with various concentrations of one of 3 different chemicals: the amino acid proline, 1-methylimidazole and 4-methylimidazole. The following components were combined in a 0.2 ml tube: 13 ml of the 2.2×PCR mix, 0.5 ml of template DNA (10 pg), 0.5 ml of a primer mix (10 mM each) and 13 ml of a 4M chemical solution (either proline, 1-methylimidazole or 4-methyl-imidazole), and the solution was mixed by pipeting. The program for PCR was: 95° C., 3 min; 30 cycles of 94° C., 30 sec; 55° C., 30 sec; 72° C., 1 min. After the PCR was done, 5 ml of loading dye was added to each tube and 12 ml of the mixture was loaded onto an agarose gel for electrophoresis followed by ethidium bromide staining of the gel for the presence of DNA fragments.

As shown in FIG. 1, certain concentrations of each of these three chemicals performed better than others. In the case of proline, 300 to 600 mM gave optimal amplification of P55G12, whereas concentrations higher than 600 mM gave no product. In the case of 1-methylimidazole, 100 and 200 mM worked best but higher or lower concentrations either did not work at all or produced much less product. In the case of 4-methylimidazole, a slightly lower range of concentration improved amplification: 60 to 100 mM. Note that without the addition of these compounds to the PCR reaction there was no amplification product, and that 1M Betaine was effective at getting the reaction to be productive.

Example 2

Titration of 4-methylmorpholine N-oxide (MMNO) for the PCR of a GC-rich Template: Comparison of MMNO and Betaine In Example 1, MMNO was identified as a novel reagent for improving PCR performance on GC-rich templates. The next issue to be addressed was the dependence of the performance of MMNO on its concentration in the PCR mix. The GC-rich amplicon P55G12 was amplified as described above in Example 1, in the presence of 1M Betaine or of various concentrations of MMNO.

Figure 2:
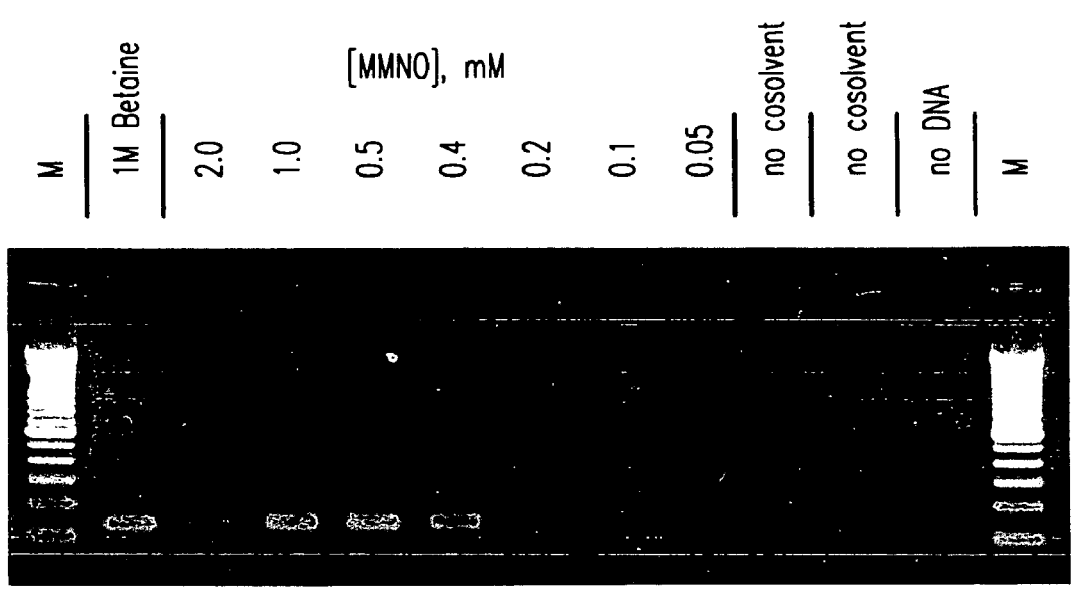
FIG. 2 is a photograph of an ethidium bromide-stained agarose gel of samples of PCR reaction mixtures amplified in the presence of the indicated concentrations of betaine or MMNO. M: DNA sizing markers.

As shown in FIG. 2, inclusion of 400 to 1000 mM MMNO in the PCR reaction mix resulted in the production of a PCR product that was comparable in intensity to that of 1M Betaine. Concentrations of MMNO lower than 400 mM did not result in the production of PCR product.

Example 3

PCR Amplification of High GC-content Amplicons: *Pseudomonas aeruginosa* Amplicons The genome of *Pseudomonas aeruginosa* contains high GC-content (70% GC) and is therefore challenging to amplify by PCR. Therefore, three different *Pseudomonas aeruginosa* amplicons ranging in size from 1.3- to 1.8-kb were tested in the PCR methods of the invention using betaine, MMNO, or trimethylamine N-oxide (TMANO) in the PCR reaction mixture. The same reaction preparation was used as described in Example 1, except that the template DNA in these reactions consisted of 30 ng of *P. aeruginosa* genomic DNA. The following PCR program was used for DNA amplification: 95° C., 5 min; 35 cycles of 94° C., 2 min, 58° C., 30 sec and 72° C., 2 min.

Figure 3:
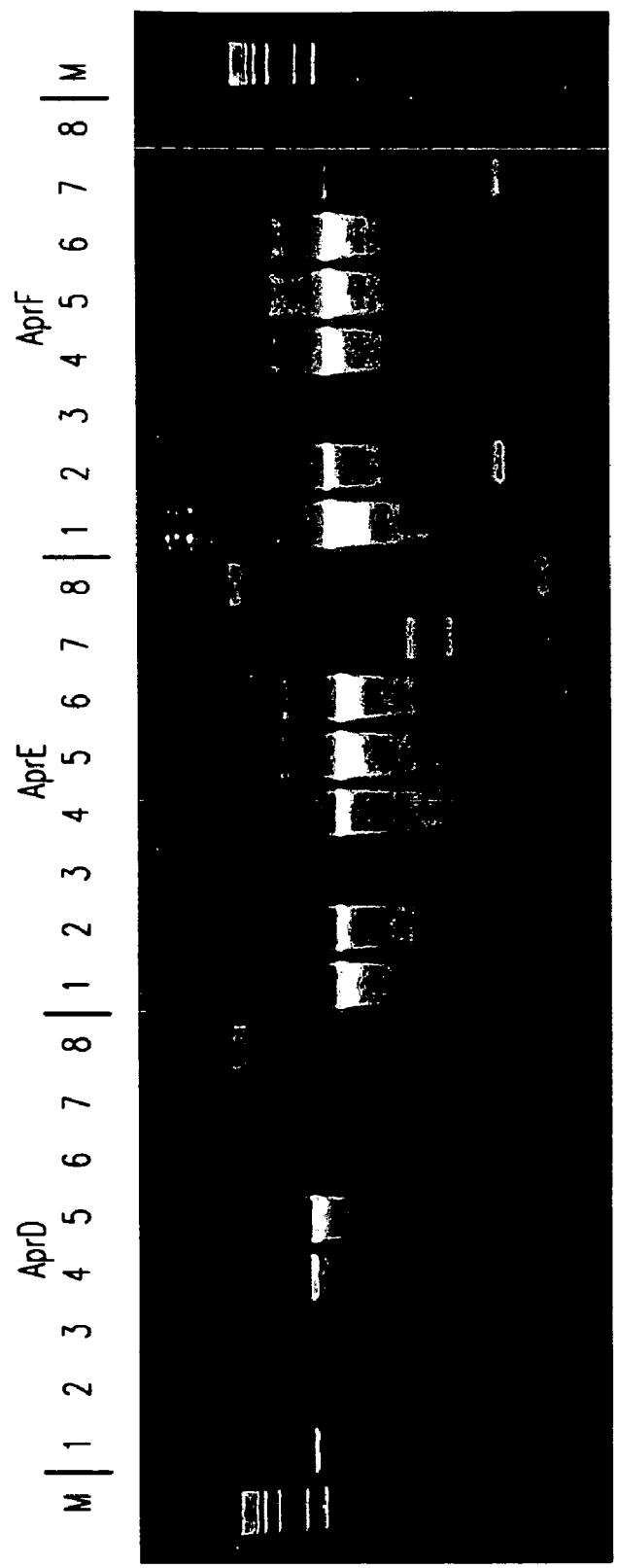
FIG. 3 is a photograph of an ethidium bromide-stained agarose gel of samples of amplifications of three different *Pseudomonas aeruginosa* amplicons (AprD, AprE, and AprF) in the presence or absence of various combinations of compounds. Lanes 1: 1 M betaine; lanes 2: 1 M TMANO; lanes 3-7: MMNO at 2 M (lanes 3), 1 M (lanes 4), 0.5 M (lanes 5), 0.4 M (lanes 6) or 0.2 M (lanes 7); lanes 8: no compound control. M: DNA sizing markers.

As shown in FIG. 3, the *Pseudomonas aeruginosa* sequence D was amplified in the presence of betaine or MMNO, whereas sequences E and F were amplified in the presence of betaine, MMNO or TMANO. These results indicate that long, natural GC-rich sequences, such as those from the genome of *P. aeruginosa*, can be efficiently amplified using the compositions and methods of the present invention.

Example 4

Comparison of Betaine, Proline and MMNO for Enhanced PCR Amplification of GC-rich templates Varying concentrations of betaine, proline and MMNO were examined for their efficacy of enhancing PCR amplification of a 156-bp fragment of human p53 exon 10 (62.2% GC) or the 2782-bp coding region for DNA polymerase I gene from *Deinococus radiodurans* (66.7% GC). Reaction parameters were varied to assess effects of buffer composition and magnesium concentration.

PCR amplifications were performed using thin-walled 0.2-ml tubes in 50 ml reactions containing 2.5 U Platinum Taq, either 1×Taq Buffer (20 mM Tris-HCl (pH8.4), 50 mM KCl) or 1×Taq High Fidelity Buffer (60 mM Tris-$SO_4$ (pH 8.9), 18 mM $(NH_4)_2SO_4$), 200 mM of each dNTP, and 200 nM of each primer. Magnesium concentration, either magnesium chloride (Taq Buffer reactions) or magnesium sulfate (Taq High Fidelity Buffer reactions), was varied between 1.0 and 2.5 mM. The amount of each cosolvent (betaine, MMNO, or proline) was varied as indicated in each figure. Reactions were temperature cycled using either a Perkin Elmer model 9600 or 2400 Thermal cycler. For amplification of human p53 exon 10 sequence, reactions contained 100 ng K562 human genomic DNA and were incubated at 95° C. for 1 min followed by 35 cycles of: denaturation at 95° C. for 30 s; annealing at 60° C. for 30 s, and extension at 68° C. for 1 min. For amplification of the DNA pol I gene, reactions contained 20 ng *Deinococcus radiodurans* genomic DNA and were incubated at 95° C. for 1 min followed by 35 cycles of: denaturation at 95° C. for 30 s; annealing at 55° C. for 30 s, and extension at 68° C. for 3 min. 10-ml of each PCR were analyzed by agarose gel electrophoresis and ethidium bromide staining for the presence of the expected DNA fragment.

Figure 4:
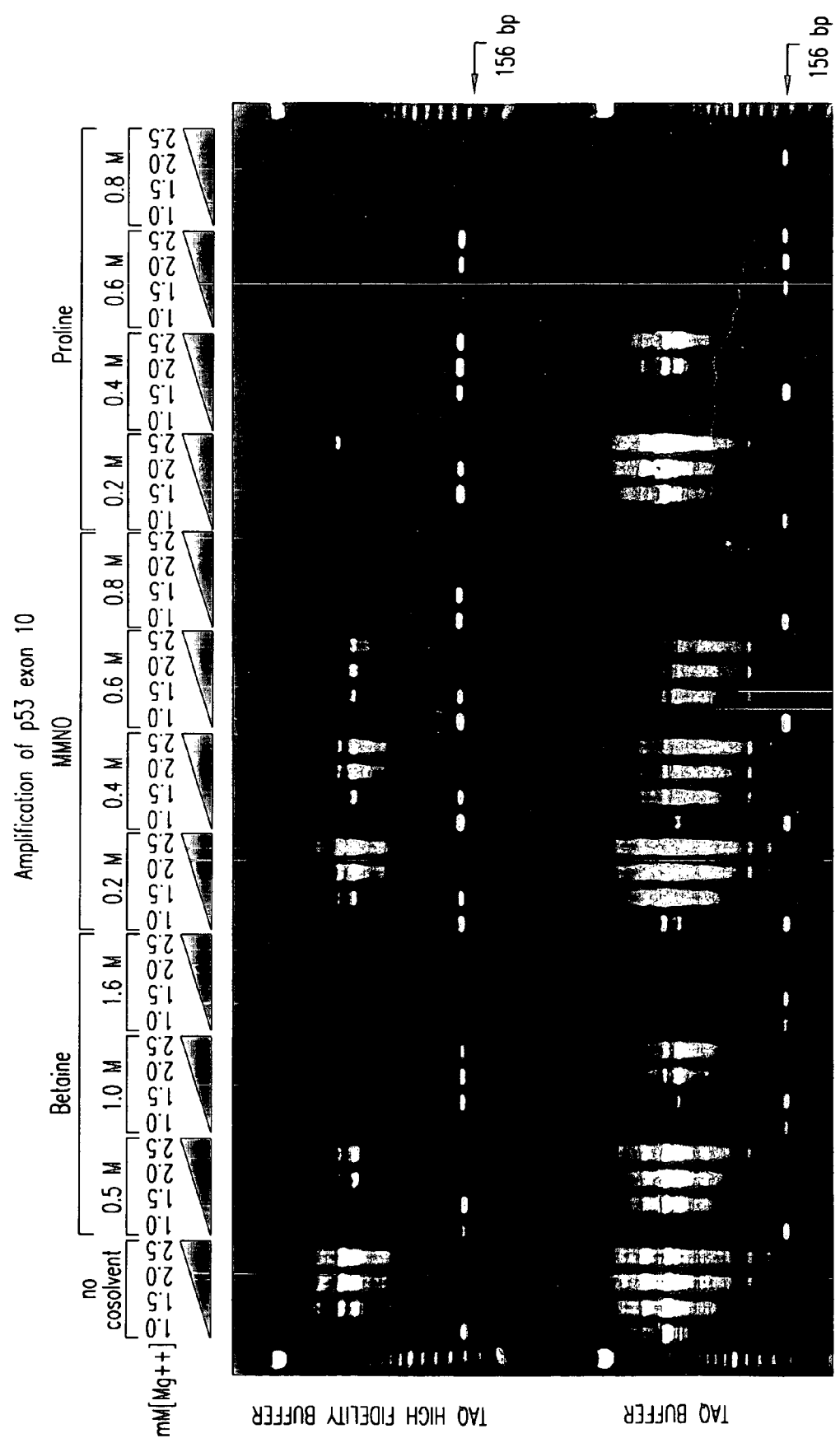
FIG. 4 is a photograph of an ethidium bromide-stained agarose gel of samples of PCR amplification of p53 exon 10 in the presence or absence of the indicated concentrations of betaine, MMNO, or proline, under different reaction buffer conditions.

As shown in FIG. 4, successful amplification of the 156-bp human p53 sequence was dependent on magnesium concentration and specific buffer conditions. In the absence of added cosolvent, specific product was not detected in reactions containing standard PCR buffer and was detectable in PCRs with ammonium sulfate buffer (Taq high fidelity buffer) only at 1.0 mM $MgSO_4$. The addition of betaine, MMNO, or proline cosolvent improved the specificity and yield of amplification product over a broader magnesium concentration in both buffer systems. The effect of MMNO on the range of optimal magnesium concentration was less pronounced than that of either betaine or proline. Concentrations of betaine or proline which produced broad magnesium optima were higher in Taq buffer than in Taq high fidelity buffer.

Figure 5:
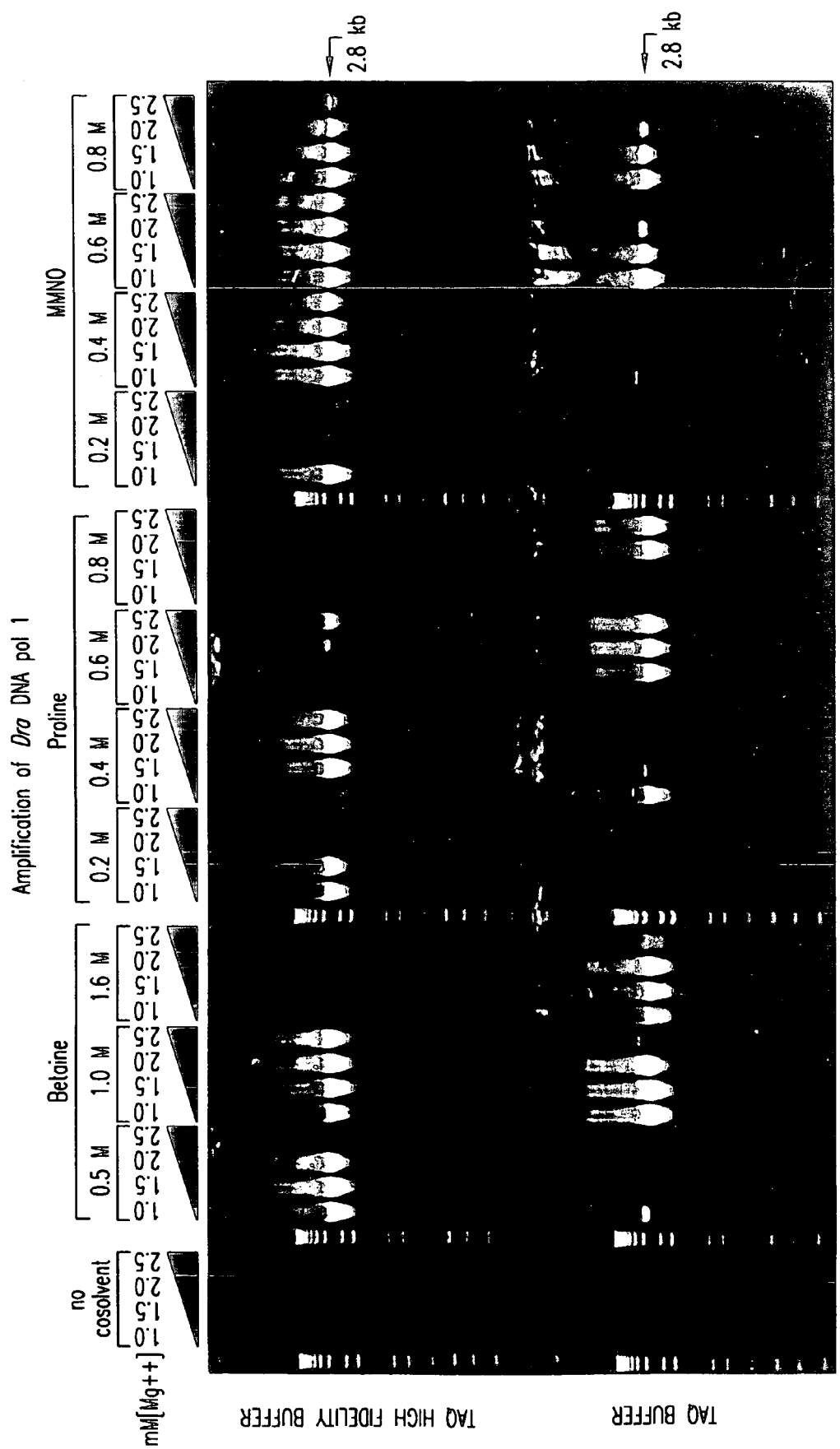
FIG. 5 is a photograph of an ethidium bromide-stained agarose gel of samples of PCR amplification of Dra DNA polymerase I in the presence or absence of the indicated concentrations of betaine, MMNO, or proline, under different reaction buffer conditions.

In contrast to results obtained with amplification of p53 exon 10, MMNO was highly effective at enhancing PCR of the longer 2.8-kb amplicon for Dra DNA polI over a broad magnesium concentration range of 1.0-2.5 mM (FIG. 5). This effect was obtained for concentrations of MMNO between 0.4 and 0.8 M and were similar to those observed for 1 M betaine. Addition of proline was also effective at enhancing amplification of the DNA polI fragment; however, the effective concentration range for proline was much narrower, and its effect on magnesium concentration range was less pronounced than that observed for betaine or MMNO. In general, higher concentrations of each cosolvent were required to enhance PCR in standard Taq buffer reaction than in reactions containing Taq high fidelity buffer. This is consistent with results obtained for amplification of p53 exon 10. Dra DNA polI PCR product was not observed in reactions which did not contain cosolvent.

Example 5

Mixtures of MMNO and Proline Enhance PCR Amplification of GC-rich Templates

Since the results of the foregoing Examples demonstrated that proline was highly effective at enhancing reaction optima for amplification of short GC-rich templates and MMNO was effective at enhancing amplification of long GC-rich templates, mixtures of the two compounds were examined to see if they would provide enhanced amplification of GC-rich templates independent of fragment size. To test this possibility, GC-rich templates were amplified in the presence of compositions comprising proline, MMNO, or both.

In mixture compositions, 4 M solutions of MMNO and proline were combined in ratios of 3:1, 2:1, 1:1, 1:2, and 1:3 respectively, to compose 4M hybrid cosolvent mixtures. These mixtures were then assayed for their effect on PCR amplification of p53 exon 10 and Dra DNA pol I. PCR reactions were performed in 50-ml volumes with Platinum Taq DNA polymerase in 1×Taq high fidelity buffer as described above. Magnesium sulfate concentration was varied between 1.0 to 2.5 mM for each concentration of cosolvent tested. Concentrations of MMNO, mixtures of MMNO and proline, proline, and betaine are as indicated in each figure.

Figure 6:
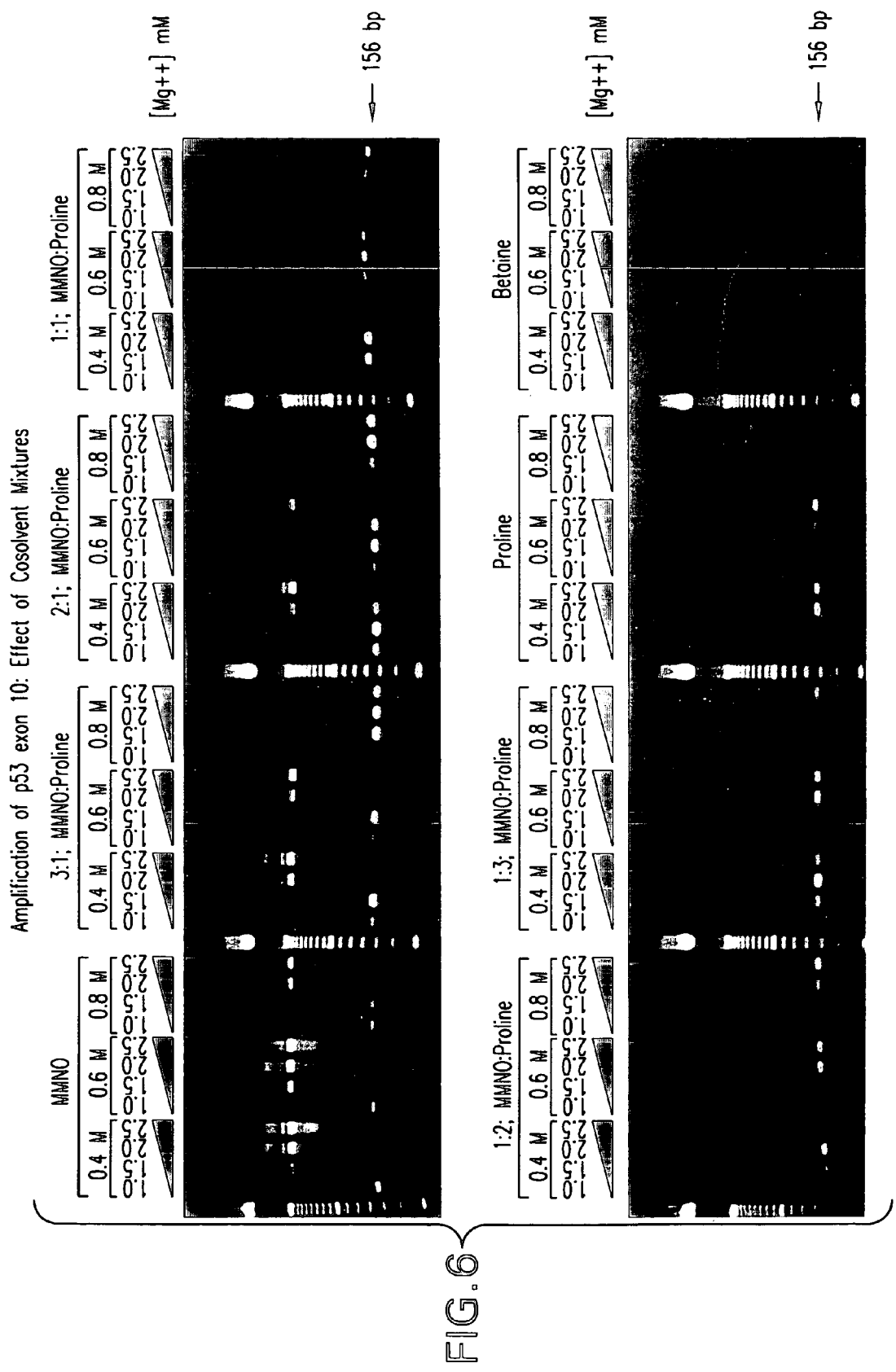
FIG. 6 is a photograph of an ethidium bromide-stained agarose gel of samples of PCR amplification of p53 exon 10 in the presence or absence of mixtures of MMNO and proline at different ratios, or in the presence of MMNO, proline, or betaine alone, under different reaction buffer conditions ($Mg^{++}$ concentrations).
Figure 7:
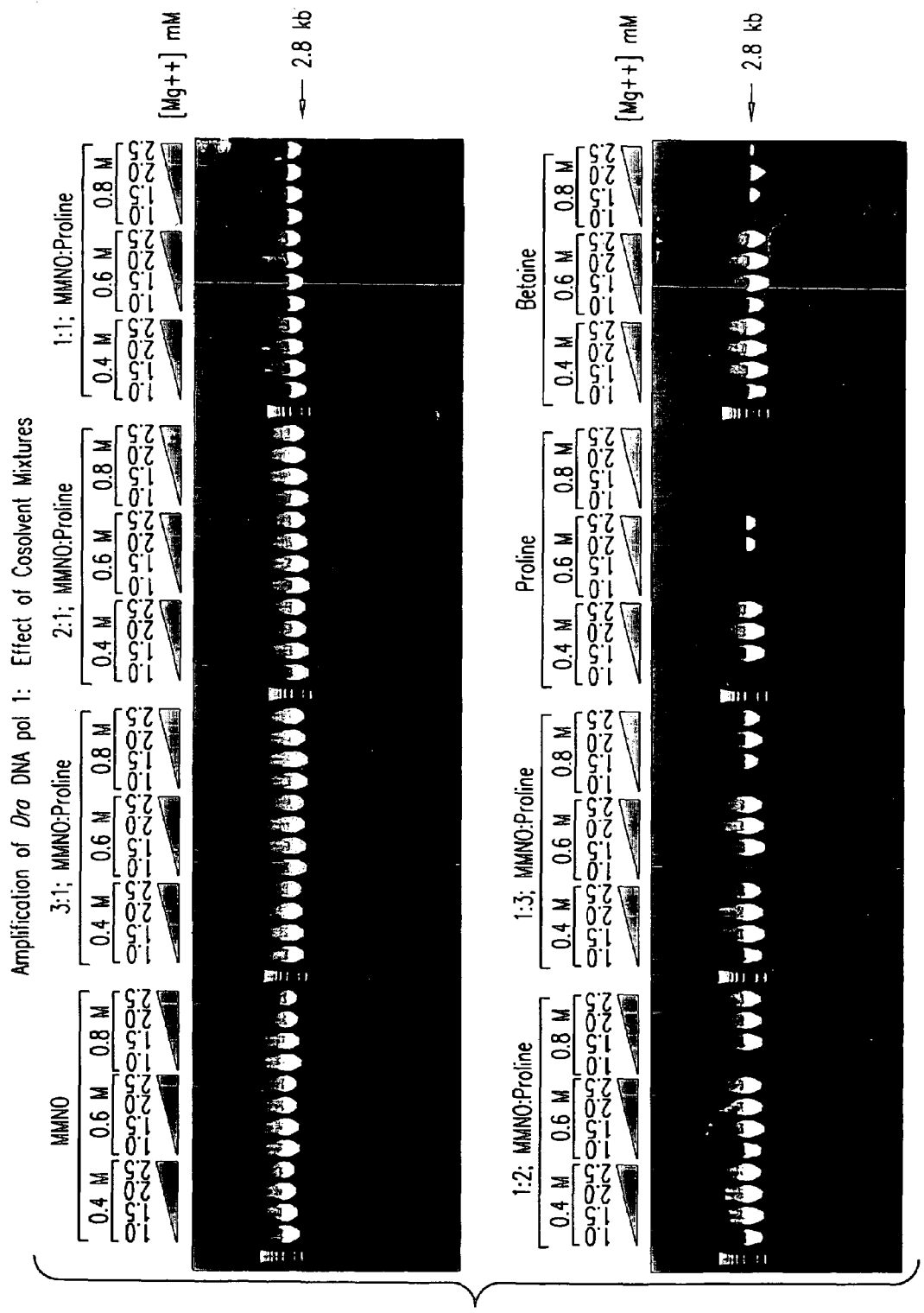
FIG. 7 is a photograph of an ethidium bromide-stained agarose gel of samples of PCR amplification of Dra DNA polymerase I in the presence or absence of mixtures of MMNO and proline at different ratios, or in the presence of MMNO, proline, or betaine alone, under different reaction buffer conditions ($Mg^{++}$ concentrations).

As shown in FIG. 6, mixtures of MMNO and proline were effective at enhancing specific amplification of the 156-bp p53 exon 10 fragment over a broader magnesium and cosolvent concentration range than that which was obtained with either cosolvent alone. Use of MMNO:proline mixtures were also highly effective at facilitating amplification of the 2.8-kb Dra DNA polI fragment and significantly extended the effective magnesium and cosolvent concentration range over that obtained with proline alone (FIG. 7). As was previously observed, MMNO enhanced PCR amplification over the full range of magnesium and cosolvent concentration tested. Collectively, these results demonstrate that the use of compositions comprising mixtures of N-alkyl carboxylic acids and N-alkyl amine oxides results in novel properties which can be exploited to enhance PCR amplification of GC-rich templates. Specifically, mixtures of MMNO and proline combined in ratios from 2:1 to 1:2 can be used to enhance PCR amplification of GC-rich templates over a broad size range and increase the reliability of PCR over broader magnesium concentrations.

Example 6

MMNO:proline Mixtures Enhance PCR of GC-rich Templates Over a Broad Annealing Temperature Optimum To assess the effects of PCR cosolvents on optimal annealing temperature during the PCR reaction, the GC-rich template P32D9 was amplified by PCR using the above-described MMNO:proline mixture compositions. PCR reactions were performed in 50-ml volumes using thin-walled 0.2-ml tubes (Stratagene, Inc.) in 50-ml reactions containing 2.5 U Platinum Taq, 1×Taq High Fidelity Buffer (60 mM Tris-SO$_4$ (pH 8.9), 18 mM (NH$_4$)$_2$SO$_4$), 1.5 mM MgSO$_4$, 200 mM each dNTP, 200 nM each primer, 100 ng K562 human genomic DNA, and either or no added cosolvent, 0.5 M betaine, or 0.5 M 1:1, MMNO:proline. Concentrated MMNO:proline mixtures were prepared by mixing equal volumes of 4 M MMNO and 4 M proline. Annealing temperature optima were studied using a gradient block Robo-cycler (Stratagene) with a heated lid for oil-free operation. Following a 1 min denaturation at 95° C., reactions were cycled 35 times at 95° C., 45 s; 55°-66° C., 45 s, 68° C., 1 min. 10-ml of each PCR was analyzed by agarose gel electrophoresis (1% Agarose 1000, Life Technologies, Inc.) in 0.5×TBE and ethidium bromide staining.

Figure 8:
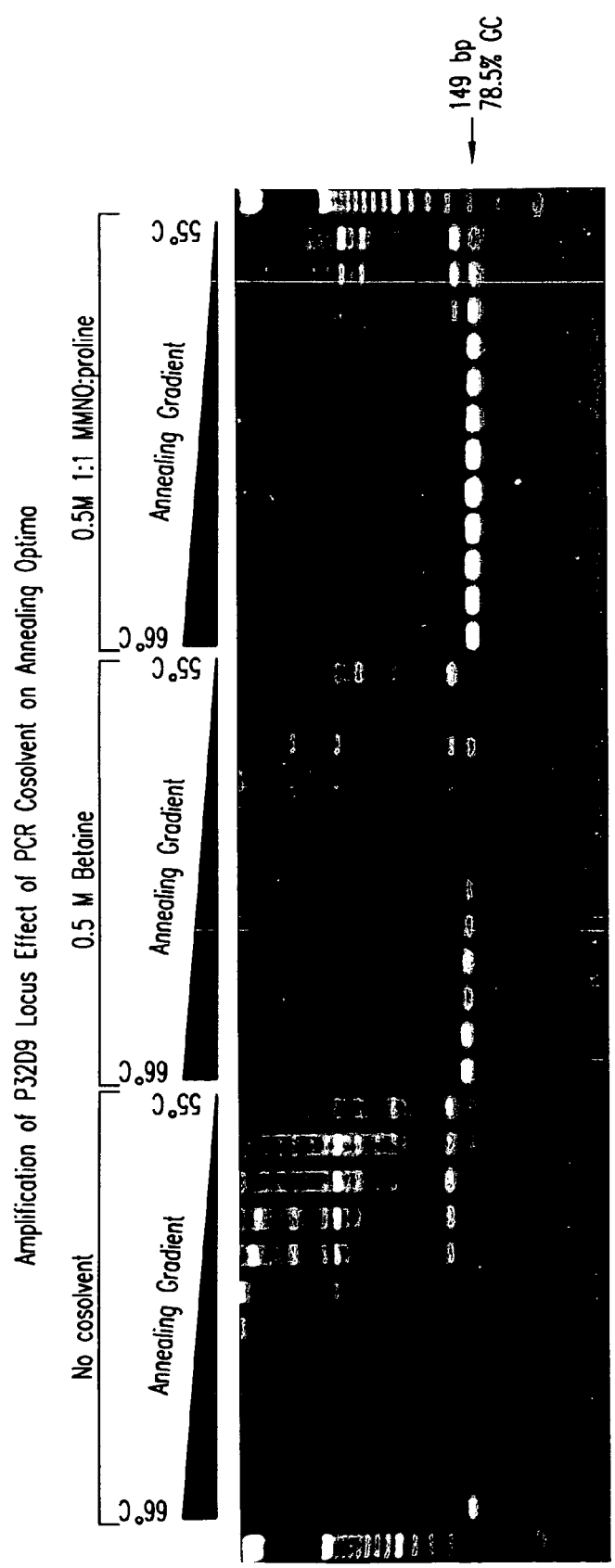
FIG. 8 is a photograph of an ethidium bromide-stained agarose gel of samples of PCR amplification of the GC-rich P32D9 template demonstrating the effects of mixtures of MMNO and proline, or of betaine, on annealing temperature optima.

As shown in FIG. 8, in the absence of PCR cosolvent specific PCR product, a 149-bp, 78.5%GC fragment, was obtained only at 66° C. Product yield rapidly diminished resulting in amplification of non-specific product as annealing temperature was decreased. In contrast, both betaine and MMNO:proline mixture extended the effective annealing temperature range. Use of MMNO:proline mixture generated higher product yield than that obtained with betaine and permitted detection of specific product over the entire 66° to 55° C. annealing temperature gradient.

Example 7

Figure 9:
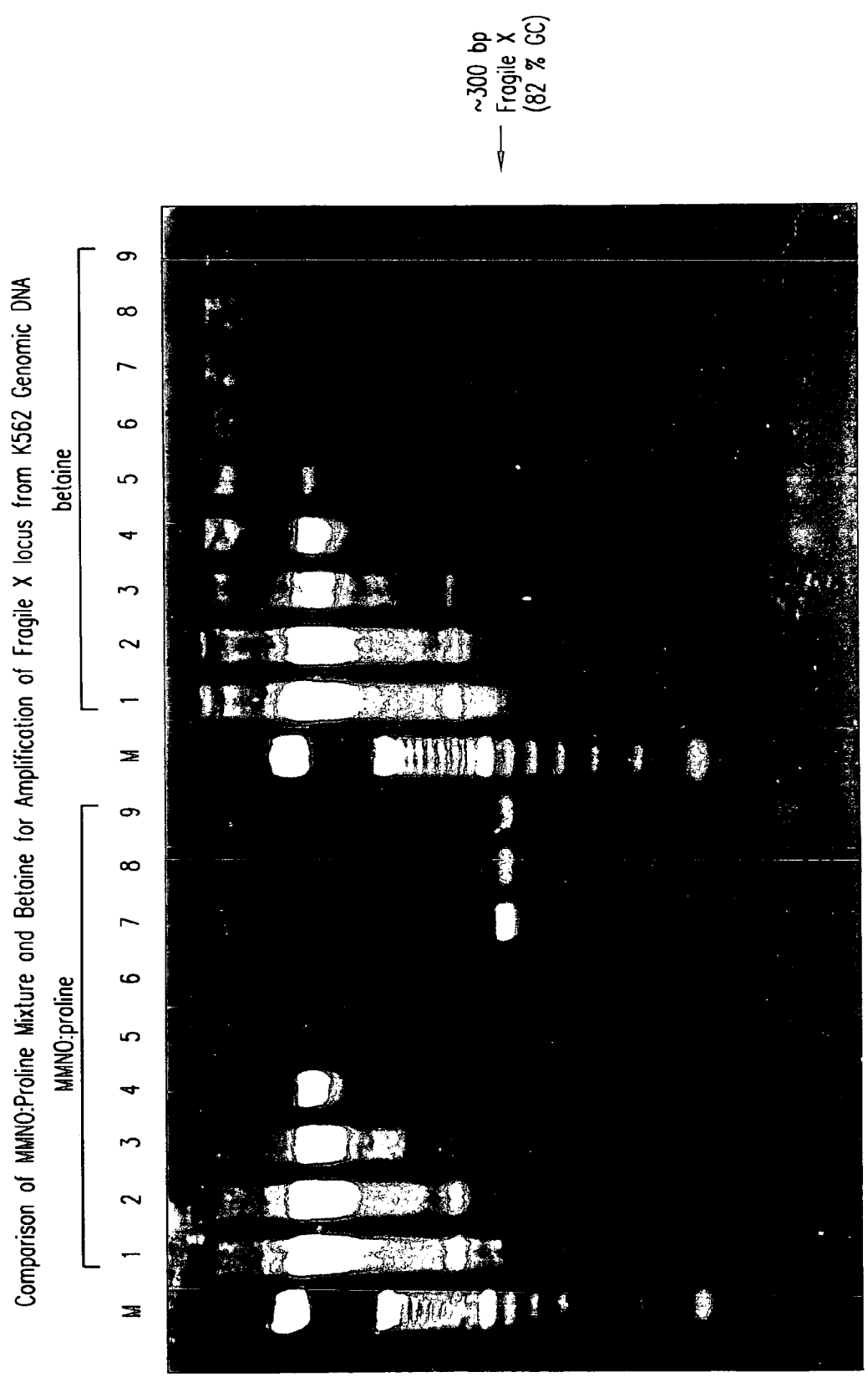
FIG. 9 is a photograph of an ethidium bromide-stained agarose gel of samples of PCR amplification of the Fragile X locus from genomic DNA of the K562 cell line in the presence of various concentrations of either betaine or of 1:1 mixtures of MMNO and proline. Lanes 1: no cosolvent; lanes 2: 0.25M; lanes 3: 0.5M; lanes 4: 0.75M; lanes 5: 1 M; lanes 6: 1.25 M; lanes 7: 1.5 M; lanes 8: 1.75 M; lanes 9: 2 M. M: DNA sizing markers.

Use of MMNO:proline Mixture for Amplification of the Fragile X CGG Repeat Sequence MMNO:proline mixture was compared to betaine for its ability to facilitate PCR amplification of very high GC content DNA sequence. Primers were designed which bracketed the CGG repeat sequence of the human FMR-1 gene in the fragile X locus (GenBank Accession No. X61378). PCR amplifications were performed as described above, using 2.5U Platinum Taq DNA polymerase high fidelity, 100 ng K562 genomic DNA and 1×Taq high fidelity buffer supplemented with 2 mM magnesium sulfate (final concentration). Aliquots of a 4M MMNO:proline mixture prepared as described above, or 4 M betaine, were added to PCRs in varying amounts to produce 0.25 M to 2 M final concentration of either cosolvent. PCRs were incubated at 95° C. for 1 min., followed by 35 cycles of: 95° C., 30 s; 58° C., 30 s; 68° C., 30 s. Agarose gel analysis of the results of these studies is shown in FIG. 9.

The results of these studies demonstrate the superior ability of MMNO:proline mixture, as compared to betaine, to facilitate PCR amplification of extremely high (>80%) GC content target sequences. In the absence of PCR cosolvent, no specific PCR product was detected. However, a faint band of the expected size was visible in reactions containing 1.75 M betaine. In contrast, robust amplification of the CGG repeat sequence was demonstrated in reactions containing 1.5 to 2 M MMNO:proline.

Example 8

Use of MMNO:proline Mixtures in Long PCR

DNA polymerase mixtures composed of Taq DNA polymerase and an archaebacterial DNA polymerase possessing proof-reading activity have been used for amplification of DNA fragments up to 40-kb (Barnes, W. M., *Proc. Natl. Acad. Sci. USA* 91:2216-2220 (1994)). The ability of MMNO:proline mixture to facilitate amplification of long GC-rich sequences was tested using primers designed to amplify 7.77-kb or 9.75-kb fragments of adenovirus type 2 DNA (~60% GC). PCRs were performed using 1 pg of adenovirus type 2 DNA (Life Technologies, Inc.), 1×Taq high fidelity buffer supplemented 1.5 mM magnesium sulfate, and varying amounts (0 to 1M) of MMNO:proline mixture essentially as described above except that 2.5U Platinum Taq DNA polymerase high fidelity, an enzyme blend of DNA polymerase from *Thermus aquaticus* and *Pyrococcus* species GB-D, was substituted for Platinum Taq DNA polymerase. Reactions were incubated for 1 min at 95° C., followed by 35 cycles of: 95° C., 30 s, 58° C., 30 s, 68° C., 10 min.

Figure 10:
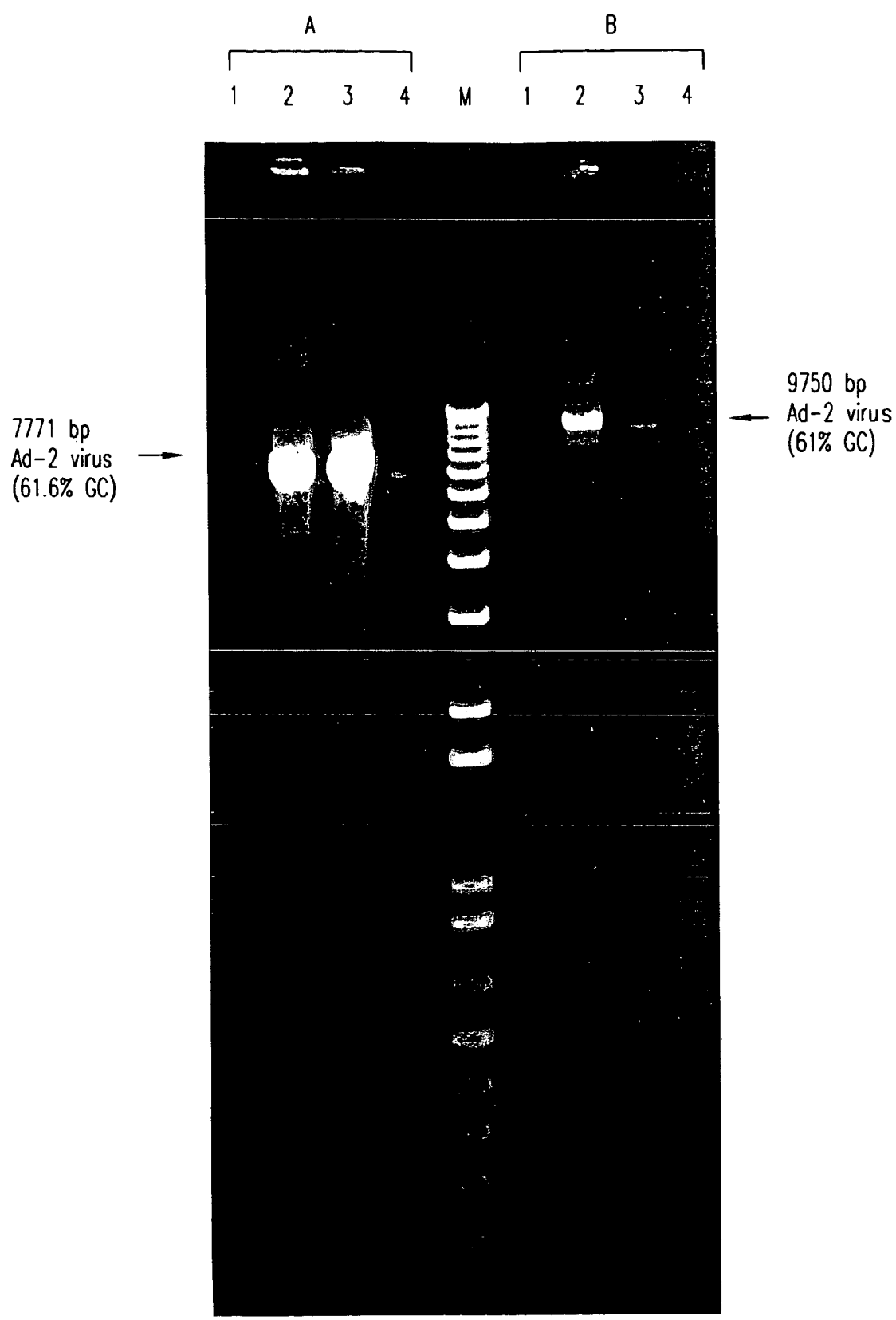
FIG. 10 is a photograph of an ethidium bromide-stained agarose gel of samples of PCR amplification of two different long GC-rich adenovirus DNA fragments in the presence or absence of different concentrations of 1:1 mixtures of MMNO and proline. Lanes 1: no cosolvent; lanes 2: 0.25 M; lanes 3: 0.5 M; lanes 4: 1.0 M. M: DNA sizing markers.

As shown in FIG. 10, successful amplification of the expected 7.77-kb and 9.75-kb DNA fragments was dependent on inclusion of MMNO:proline cosolvent. Specific product was not detected in reactions without MMNO:proline; however, robust amplification and high product yield was obtained by inclusion of 0.25 M MMNO:proline mixture. Product yield in long PCR was sensitive to the amount of MMNO:proline used as product yield for both the 7.3 and 9.7-kb target decreased with increasing MMNO:proline concentration.

Example 9

Comparison of Compensatory Solutes to Enhance PCR Amplification of GC Rich Templates A wide variety of amino compounds have been shown to serve a critical function in protecting organisms from osmotic stress. Betaine and proline are the major osmoprotectants in *E. coli*. Since both these compounds disrupt DNA helix stability and thereby facilitate amplification of GC rich templates, the effects of other known and commercially available osmoregulatory compounds in PCR were investigated.

PCR mixtures were prepared in a volume of 50 ml, containing 2.5 U Platinum Taq DNA polymerase, 60 mM Tris-SO$_4$ (pH 8.9), 18 mM (NH4)$_2$SO$_4$,1.5 mM MgSO$_4$, 200 mM dNTP (each), 200 nM primer (each), 100 ng K562 human genomic DNA and varying amounts of PCR cosolvents were prepared. Reactions were incubated at 95° C. for 1 min, followed by 35 cycles of: 95° C., 30 s; 58° C., 30 s; 68° C., 1 min.

Figure 11:
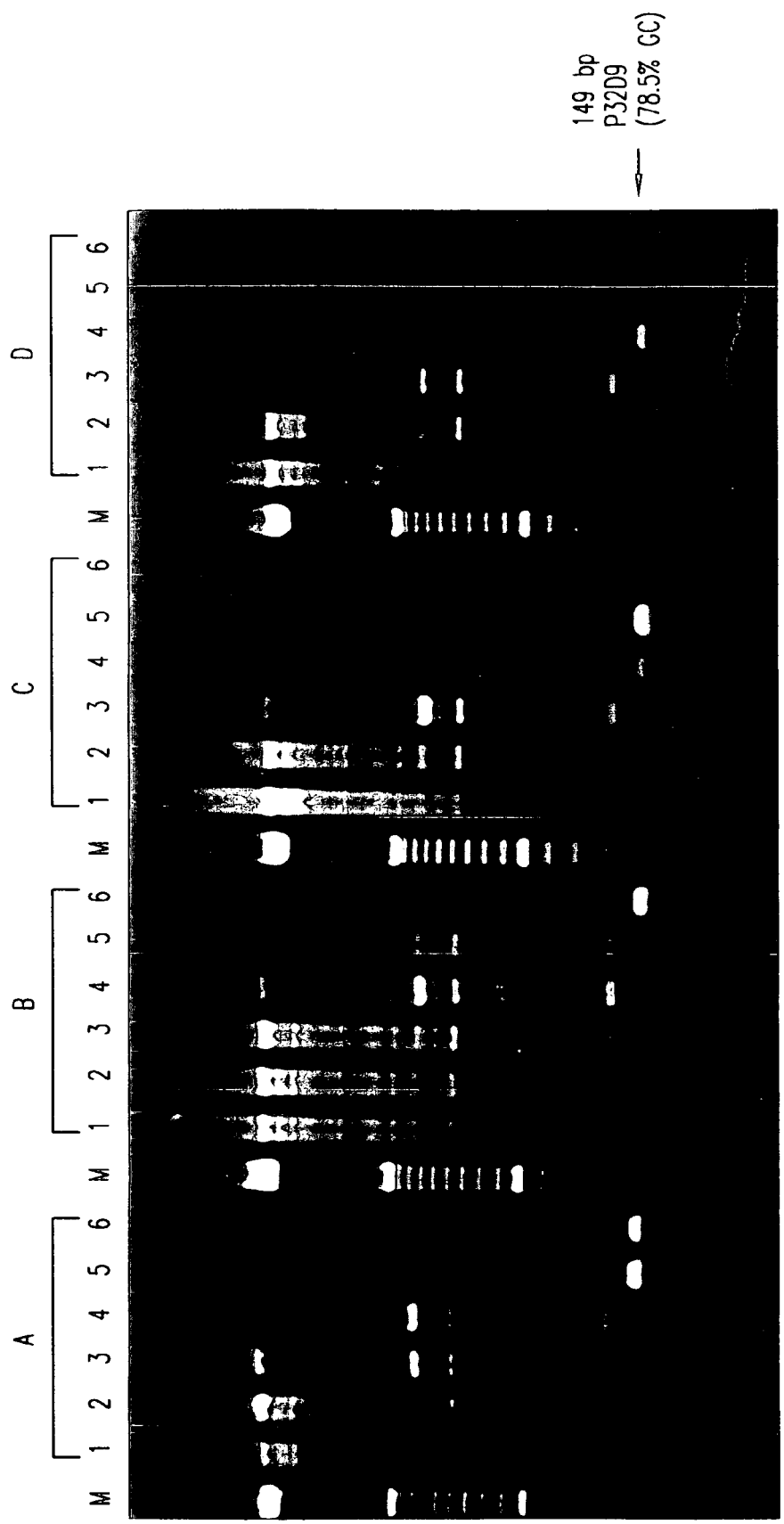
FIG. 11 is a photograph of an ethidium bromide-stained agarose gel of samples of PCR amplification of GC-rich fragments of K562 genomic DNA in the presence or absence of various concentrations of 1:1 mixtures of MMNO and proline (lanes A), betaine (lanes B), L-carnitine (lanes C) or DL-pipecolic acid (lanes D). Lanes 1: no cosolvent; lanes 2: 0.25 M; lanes 3: 0.5 M; lanes 4: 1 M; lanes 5: 1.5 M; lanes 6: 2 M. M: DNA sizing markers.
Figure 12:
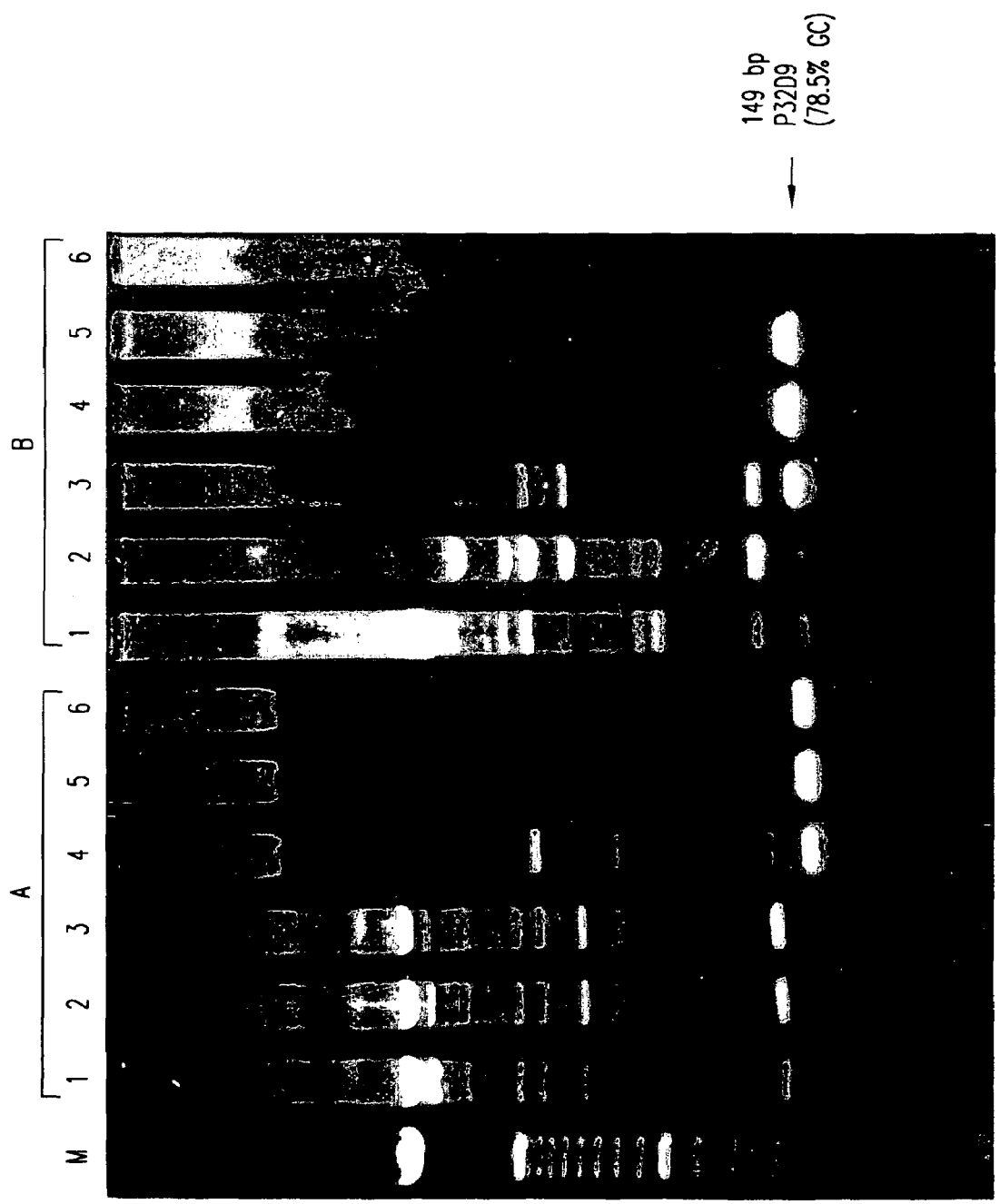
FIG. 12 is a photograph of an ethidium bromide-stained agarose gel of samples of PCR amplification of GC-rich fragments of K562 genomic DNA in the presence or absence of various concentrations of betaine (lanes A) or ectoine (lanes B). Lanes 1: no cosolvent; lanes 2: 0.25 M; lanes 3: 0.5 M; lanes 4: 1 M; lanes 5: 1.5 M; lanes 6: 2 M. M: DNA sizing markers.
Figure 13:
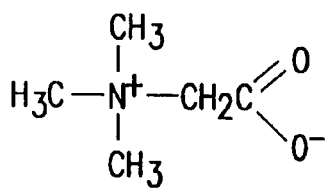
FIG. 13 shows the structures of a number of example compounds that may be used in accordance with the invention.
Figure 13:
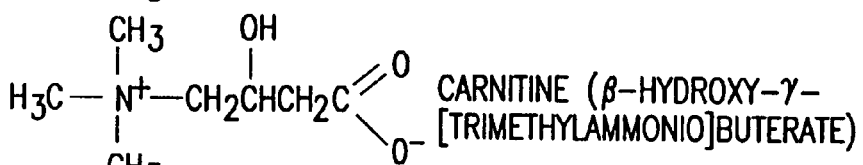
Figure 13:
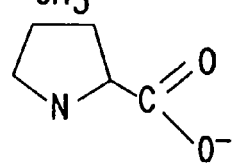
Figure 13:
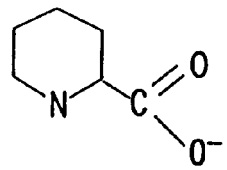
Figure 13:
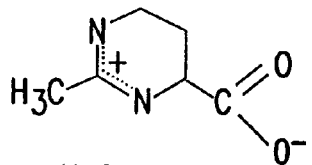
Figure 13:
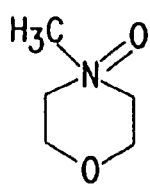
Figure 13:
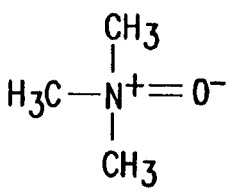
Figure 13:
Figure 13:
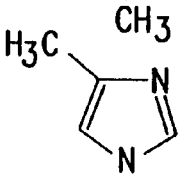

Comparison of the efficacy of MMNO:proline mixture, betaine, L-camitine; and DL-pipecolic acid are shown in FIG. 11, while the results of a separate experiment in which ectoine was compared to betaine are shown in FIG. 12. Experimental conditions were essentially the same as those described above except that the final reaction volume was 25 ml.

All of the osmolytes examined in these experiments were effective at enabling amplification of the P32D9 sequence and demonstrate that a wide variety of N-alkyl carboxylic acid derivatives can be used to facilitate PCR amplification of difficult templates, such as templates that are high in GC content.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing a polypeptide, comprising:
   (a) mixing a nucleic acid template with one or more compounds having a chemical formula selected from the group consisting of formula I or formula II, or a salt thereof, wherein said compound is not betaine:

Formula I:

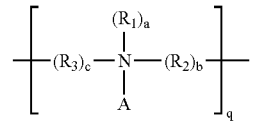

where A is

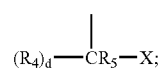

where X is

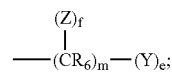

where N is positively charged;

wherein q=1 to 100,000, wherein when q=2 to 100,000 each monomer of formula I may be the same as or different from the other monomers of formula I;

wherein Z may be the same as or different from Y;

wherein each Y and Z are independently selected from the group consisting of —OH, —NH$_2$, —SH, —PO$_3$H, —CO$_2$H, —SO$_3$H and hydrogen;

wherein f is an integer from 0 to 2, m is an integer from 0 to 20 and e is an integer from 0 to 2;

wherein R$_4$, R$_5$, and R$_6$ may be the same or different and are independently selected from the group consisting of hydrogen, alkyl, alkenyl, alkynyl, aryl, amino, mercaptan, thiol, halo, nitro, nitrilo, hydroxy, hydroxyalkyl, hydroxyaryl, phosphato, alkoxy, oxide, ether, ester (alkanoyloxy), carboxy, carbonyl, sulfonyl, sulfonic and amido groups, and d is an integer from 0 to 2;

wherein a, b, and c are independently an integer from 0 to 1, with the proviso that no more than two of a, b, and c are zero;

wherein R$_1$, R$_2$ and R$_3$ may be the same or different and are independently selected from the group consisting of:

a) =O and;

b) 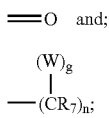

with the proviso that no more than two of A, $R_1$, $R_2$ and $R_3$ are selected from the group consisting of hydrogen, methyl, ethyl and propyl; and with the proviso that if one, and only one, of $R_1$, $R_2$ and $R_3$ is =O, then A is none of hydrogen, methyl, ethyl and propyl;

wherein each $R_7$ and W may be the same or different and are independently selected from the group consisting of hydrogen, alkyl, alkenyl, alkynyl, aryl, amino, thiol, mercaptan, halo, nitro, nitrilo, hydroxy, hydroxyalkyl, hydroxyaryl, phosphato, alkoxy, oxide, ether, ester (alkanoyloxy), carboxy, carbonyl, sulfonyl, sulfonic and amido groups; g is an integer from 0 to 2 and n is an integer from 0 to 20, with the proviso that if two of $R_1$, $R_2$, and $R_3$ are =O, then the other is not =O;

Formula II:

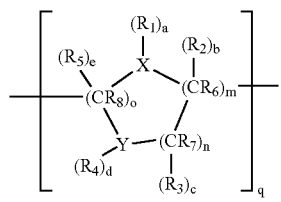

wherein Formula II is saturated or unsaturated;

wherein q=1 to 100,000, wherein when q=2 to 100,000, each monomer of formula II may be the same as or different from each other monomer of formula II;

wherein X is selected from the group consisting of N, C, O, P and S;

wherein Y is selected from the group consisting of O, N, S, P, C, —O—NH—, —O—CH$_2$—NH—, —O—CH$_2$—O—, —NH—CH$_2$—NH—, —O—CH(CH$_3$)—NH—, —NH—CH(CH$_3$)—NH—, —O—CH(CH$_3$)—O—, —NH—C(CH$_3$)$_2$—NH—, —O—S—, —O—CH$_2$—S—, —NH—S—, —NH—CH$_2$—S—, and other mercaptan, phosphato, alkoxy, oxide, ether, esters (alkanoyloxy), carboxy, sulfonyl, sulfonic and amido groups;

with the proviso that if either X or Y is N, then the other is not C;

wherein $R_1$, $R_2$, $R_3$, $R_4$, $R_5$, $R_6$, $R_7$ and $R_8$ may be the same or different and are independently selected from the group consisting of hydrogen, alkyl, alkenyl, alkynyl, aryl, amino, thiol, mercaptan, halo, nitro, nitrilo, hydroxy, hydroxyalkyl, hydroxyaryl, phosphato, alkoxy, oxide, ether, ester (alkanoyloxy), carboxy, sulfonyl, sulfonic and amido groups; and wherein a, b, c, d, e, m, n and o are integers which may be the same or different and are independently selected from 0 to 2 for a, b, c, d, and e, and 0 to 5 for m, n and o, to form a mixture;

(b) incubating the mixture under conditions whereby a first nucleic acid molecule complementary to all or a portion of the template and encoding at least one polypeptide is made;

(c) inserting one or more of the first nucleic acid molecules into a host cell; and (d) expressing the polypeptide encoded by the first nucleic acid molecule in the host cell.

2. The method of claim 1, further comprising isolating the polypeptide from the host cell.

3. The method of claim 1, wherein the bases of the nucleic acid template comprise greater than about 60% guanine and cytosine.

4. The method of claim 1, wherein said insertion occurs via calcium phosphate transfection, DEAE-dextran mediated transfection, cationic lipid-mediated transfection, electroporation, transduction or infection.

5. The method of claim 1, further comprising cloning the first nucleic acid molecule into a vector or plasmid prior to insertion into the host cell.

6. The method of claim 2, wherein said isolation occurs via ammonium sulfate precipitation, ethanol precipitation, electrophoresis, immunoadsorption or chromatography.

7. The method of claim 1, wherein the host cell is an *Escherichia coli* host cell.

8. A method for producing a polypeptide, comprising:

(a) mixing a nucleic acid template with one or more compounds having a chemical formula selected from the group consisting of 1-methylimidazole, 4-methylimidazole, 4-methylmorpholine N-oxide, poly(2-ethyl-2-oxazoline) of average molecular weight about 50,000 to about 500,000 daltons and poly(diallyldimethylammonium chloride) of average molecular weight about 100,000 to about 200,000 daltons;

(b) incubating the mixture under conditions whereby a first nucleic acid molecule complementary to all or a portion of the template and encoding at least one polypeptide is made;

(c) inserting one or more of the first nucleic acid molecules into a host cell; and (d) expressing the polypeptide encoded by the first nucleic acid molecule in the host cell.

9. The method of claim 8, further comprising isolating the polypeptide from the host cell.

10. The method of claim 8, wherein the bases of the nucleic acid template comprise greater than about 60% guanine and cytosine.

11. The method of claim 8, wherein said insertion occurs via calcium phosphate transfection, DEAE-dextran mediated transfection, cationic lipid-mediated transfection, electroporation, transduction or infection.

12. The method of claim 8, further comprising cloning the first nucleic acid molecule into a vector or plasmid prior to insertion into the host cell.

13. The method of claim 9, wherein said isolation occurs via ammonium sulfate precipitation, ethanol precipitation, electrophoresis, immunoadsorption or chromatography.

14. The method of claim 8, wherein the host cell is an *Escherichia coli* host cell.

* * * * *